(12) United States Patent
Vasudevan et al.

(10) Patent No.: US 9,434,666 B2
(45) Date of Patent: Sep. 6, 2016

(54) CATALYTIC HYDROGENATION USING COMPLEXES OF BASE METALS WITH TRIDENTATE LIGANDS

(75) Inventors: Kalyan V. Vasudevan, Los Alamos, NM (US); Guoqi Zhang, Los Alamos, NM (US); Susan K. Hanson, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 1057 days.

(21) Appl. No.: 13/587,717

(22) Filed: Aug. 16, 2012

(65) Prior Publication Data

US 2015/0336862 A1  Nov. 26, 2015

(51) Int. Cl.
| | |
|---|---|
| *C07C 29/145* | (2006.01) |
| *C07C 67/303* | (2006.01) |
| *C07C 51/36* | (2006.01) |
| *C07C 41/18* | (2006.01) |
| *C07C 41/01* | (2006.01) |
| *C07C 41/20* | (2006.01) |
| *C07C 45/62* | (2006.01) |
| *C07C 209/52* | (2006.01) |
| *C07C 5/03* | (2006.01) |
| *C07C 5/05* | (2006.01) |
| *C07C 231/24* | (2006.01) |
| *C07F 15/04* | (2006.01) |
| *C07F 15/06* | (2006.01) |
| *C07F 5/04* | (2006.01) |
| *C07D 211/46* | (2006.01) |
| *C07C 29/17* | (2006.01) |
| *C07C 17/354* | (2006.01) |
| *C07C 29/141* | (2006.01) |
| *C07C 41/26* | (2006.01) |
| *C07D 211/02* | (2006.01) |
| *B01J 31/18* | (2006.01) |

(52) U.S. Cl.
CPC ............ *C07C 29/172* (2013.01); *B01J 31/189* (2013.01); *C07C 5/03* (2013.01); *C07C 5/05* (2013.01); *C07C 17/354* (2013.01); *C07C 29/141* (2013.01); *C07C 29/145* (2013.01); *C07C 29/175* (2013.01); *C07C 41/01* (2013.01); *C07C 41/18* (2013.01); *C07C 41/20* (2013.01); *C07C 41/26* (2013.01); *C07C 45/62* (2013.01); *C07C 51/36* (2013.01); *C07C 67/303* (2013.01); *C07C 209/52* (2013.01); *C07D 211/02* (2013.01); *C07D 211/46* (2013.01); *C07F 5/04* (2013.01); *C07F 15/04* (2013.01); *C07F 15/045* (2013.01); *C07F 15/06* (2013.01); *C07F 15/065* (2013.01); *B01J 2231/643* (2013.01); *B01J 2531/0244* (2013.01); *B01J 2531/845* (2013.01); *B01J 2531/847* (2013.01); *C07C 2101/14* (2013.01); *C07C 2101/16* (2013.01); *C07C 2101/18* (2013.01); *C07C 2102/08* (2013.01); *C07C 2102/42* (2013.01); *C07C 2103/18* (2013.01); *C07C 2531/14* (2013.01); *C07C 2531/28* (2013.01)

(58) Field of Classification Search
None
See application file for complete search history.

(56) References Cited

PUBLICATIONS

Rozenel et al., 40(40) Dalton Trans. 10397-10405 (2011).*
Angulo et al., "New nickel-containing homogeneous hydrogenation catalysts Structures of [Ni(o-MeO-dpppol)Cl2] and [Ni(dcpe)Cl2]," Journal of Molecular Catalysis A: Chemical 202:97-106, 2003.
Appel et al., "[Ni(PPh2NBn2)2(CH3CN)]2+ as an Elecgtrocatalyst for H2 Production: Dependence on Acid Strength and Isomer Distribution," ACS Catalyst 1:777-785, 2011 (published online Apr. 22, 2011).
Balaraman et al., "Direct Hydrogenation of Amides to Alcohols and Amines under Mild Conditions," Journal of the American Chemical Society, 132:16756-16758, 2010 (published online Nov. 4, 2010).
Balogh-Hergovich et al., "Kinetics of the Homogeneous Hydrogenation of Cyclohexene Catalyzed by Hydridocobalt Complexes Formed in situ from CoH(N2)(PPh3)3," Journal of Organometallic Chemistry 66:303-310, 1974.
Bart et al., "Preparation and Molecular and Electronic Structures of Iron(0) Dinitrogen and Silane Complexes and Their Application to Catalytic Hydrogenation and Hydrosilation," Journal of the American Chemical Society 126:13794-13807, 2004 (published online Oct. 5, 2004).
Berkefeld et al., "Deactivation Pathways of Neutral NI(II) Polymerization Catalysts," Journal of the American Chemical Society 131:1565-1574, 2009 (published online Jan. 12, 2009).
Bianchini et al., "Electrochemistry as a Diagnostic Tool to Discriminate between Classical M-(H)2 and Nonclassical M-(H2) Structures within a Family of Dihydride and Dihydrogen Metal Complexes," Inorg. Chem. 29:3394-3402, 1990.
Bolig et al., "Activation of sp3 C—H Bonds with Cobalt(I): Catalytic Synthesis of Enamines," Journal of the American Chemical Society 129:14544-14545, 2007 (published online Nov. 7, 2007).
Breitenfeld et al., "Synthesis, Reactivity, and Catalytic Application of a Nickel Pincer Hydride Complex," Organometallics 31:2128-2136, 2012 (published online Feb. 22, 2012).
Brookhart et al., "[(3,5-(CF3)2C6H3)4B]-[H(OEt2)2]+: A Convenient Reagent for Generation and Stabilization of Cationic, Highly Electrophilic Organometallic Complexes," Organometallics 11(11):3920-3922, 1992.

(Continued)

*Primary Examiner* — Timothy R Rozof
(74) *Attorney, Agent, or Firm* — Lewis Roca Rothgerber Christie LLP

(57) ABSTRACT

Complexes of cobalt and nickel with tridentate ligand PNHP$^R$ are effective for hydrogenation of unsaturated compounds. Cobalt complex [(PNHP$^{Cy}$)Co(CH$_2$SiMe$_3$)]BAr$^F_4$ (PNHP$^{Cy}$=bis[2-(dicyclohexylphosphino)ethyl]amine, BAr$^F_4$=B(3,5-(CF$_3$)$_2$C$_6$H$_3$)$_4$)) was prepared and used with hydrogen for hydrogenation of alkenes, aldehydes, ketones, and imines under mild conditions (25-60° C., 1-4 atm H$_2$). Nickel complex [(PNHP$^{Cy}$)Ni(H)]BPh$_4$ was used for hydrogenation of styrene and 1-octene under mild conditions. (PNP$^{Cy}$)Ni(H) was used for hydrogenating alkenes.

19 Claims, No Drawings

(56) References Cited

PUBLICATIONS

Butts et al., "Synthesis, Structure, and Reactivity of the Remarkably Stable Early-Late Binuclear Metal Hydride Cp2Ta (μ-CH2)2Ir(Cp*)(H). A Warning Concerning Catalyst Identification in Homogeneous Catalytic Reactions," Organometallics 13(7):2668-2676, 1994.

Casey et al., "An Efficient and Chemoselective Iron Catalyst for the Hydrogenation of Ketones," Journal of the American Chemical Society 129:5816-5817, 2007 (published online Apr. 17, 2007).

Casey et al., "Iron Carbonyl Catalyzed Isomerization of 3-Ethyl-l-pentene. Multiple Olefin Isomerizations via a π-Allyl Metal Hydride Intermediate," Journal of the American Chemical Society 95(7):2248-2253, Apr. 4, 1973.

Chakraborty et al., "Catalytic properties of nickel bis(phosphinite) pincer complexes in the reduction of CO2 to methanol derivatives," Polyhedron 32:30-34, 2012 (published online May 4, 2011).

Chen et al., "Highly active iridium catalysts for the hydrogenation of ketones and aldehydes," The Royal Chemical Society 8:1407-1410, 2009 (published online Jan. 13, 2009).

Ciancanelli et al., "Comprehensive Thermodynamic Characterization of the Metal-Hydrogen Bond in a Series of Cobalt-Hydride Complexes," Journal of the American Chemical Society 124(12):2984-2992, 2002 (published online Mar. 1, 2002).

Corma et al., "Optically active complexes of transition metals (RhI, RuII, CoII and NiII) with 2-aminocarbonylpyrrolidine ligands. Selective catalysts for hydrogenation of prochiral olefins," Journal of Organometallic Chemistry 431:233-246, 1992.

Corma et al., "Chemical Routes for the Transformation of Biomass into Chemicals," Chem. Rev. 107:2411-2502, 2007 (published online May 30, 2007).

Daida et al., "Considering Fe II/IV Redox Processes as Mechanistically Relevant to the Catalytic Hydrogenation of Olefins by [PhBPiPr3]Fe-Hx Species," Inorganic Chemistry 43(23):7474-7485, 2004 (published online Oct. 14, 2004).

Deubel et al., "Challenge of the Copolymerization of Olefins with N-Containing Polar Monomers. Systematic Screening of Nickel(II) and Palladium(II) Catalysts with Brookhart and Grubbs Ligands. 2. Chain-Propagation Barriers, Intrinsic Regioselectivity, and Curtin-Hammett Reactivity," Organometallics 21(21):4432-4441, 2002 (published online Sep. 20, 2002).

Ding et al., "Three-Coordinate and Four-Coordinate Cobalt Hydride Complexes That React with Dinitrogen," Journal of the American Chemical Society 131:10804-10805, 2009 (published online Jul. 21, 2009).

Doherty et al., "Reactions of H2 and R3SiH with Electrophilic Cobalt(III) Alkyl Complexes: Spectroscopic Characterization, Dynamics, and Chemistry of [Cp*Co(L)(H)(η2-H2)][B(ArF)4] and [Cp*Co(L)(H)(η2-HSiR3)][B(ArF)4]." Organometallics 26(24):5950-5960, 2007 (published online Oct. 19, 2007).

Enthaler et al., "Sustainable Metal Catalysis with Iron: From Rust to a Rising Star?**," Angew. Chem. Int. Ed. 47:3317-3321, 2008.

Feder et al., "Mechanism of the Cobalt Carbonyl-Catalyzed Homogeneous Hydrogenation of Aromatic Hydrocarbons," Journal of the American Chemical Society 97(24):7186-7188, Nov. 26, 1975.

Federsel et al., "Catalytic Hydroenation of Carbon Dioxide and Bicarbonates with a Well-Defined Cobalt Dihydrogen Complex," Chem. Eur. J. 18:72-75, 2012.

Ferrari et al., "Catalysis by Phosphine Cobalt Carbonyl Complexes. V. Kinetics of Homogeneous Cyclohexene Hydrogenation Catalyzed by CoH(CO)2[P(n-C4H9)3]2*," Journal of Organometallic Chemistry 43:213-223, 1972.

Flores-Gaspar et al., "Selective hydrogenation of the C=O bond of ketones using Ni(0) complexes with a chelating bisphosphine," Journal of Molecular Catalysis A: Chemical 309:1-11, 2009 (published online Jun. 10, 2009).

Friedrich et al., "Highly Stereoselective Proton/Hydride Exchange: Assistance of Hydrogen Bonding for the Heterolytic Splitting of H2," Journal of the American Chemical Society 131:17552-17553, 2009 (published online Nov. 12, 2009).

Fryzuk et al., "One-Electron Transformations of Paramagnetic Cobalt Complexes. Synthesis and Structure of Cobalt (II) Amidodiphosphine Halide and Alkyl Complexes and Their Reaction with Alkyl Halides," Journal of the American Chemical Society 120:10126-10135, 1998.

Fullmer et al., "Three-Coordinate NiII: Tracing the Origin of an Unusual, Facile Si—C(sp3) Bond Cleavage in [(tBu2PCH2SiMe2)2N]Ni+," Journal of the American Chemical Society 133:2571-2582, 2011 (published online Feb. 9, 2011).

Gonzalez-Arellano et al., "Easy Synthesis of New Chiral Tridentate Schiff Bases and Their Use as [N,N,O] Ligands for Ni and Pd Complexes—Catalytic Behavior versus Hydrogenation Reactions[**]," Eur. J. Inorg. Chem. 1955-1962, 2004.

Hagen et al., "Is it Homogeneous of Heterogeneous Catalysis? Compelling Evidence for Both Types of Catalysts Derived from [Rh(η5-C5Me5)Cl2]2 as a Function of Temperature and Hydrogen Pressure," Journal of the American Chemical Society 127:4423-4432, 2005 (published online Mar. 3, 2005).

Harman et al., "Reversible H2 Addition across a Nickel-Borane Unit as a Promising Strategy for Catalysis," Journal of the American Chemical Society 134(11):5080-5082, 2012 (published online Mar. 1, 2012).

Hebden et al., "Preparation of a Dihydrogen Complex of Cobalt," Angew. Chem. Int. Ed. 50:1873-1876, 2011.

Helm et al., "A Synthetic Nickel Electrocatalyst with a Turnover Frequency Above 100,000 s-1 for H2 Production," Science 333:863-866, Aug. 12, 2011.

Hidai et al., "Hydrogenation of Olefins Using CoH3 (PPh3)3 and CoH(CO)(PPh3)3," Tetrahedron Letters 20:1715-1716, 1970.

Hsiao et al., "Organometallic Chemistry of Sulfur/Phosphorus Donor Ligand Complexes of Nickel(II) and Nickel(0)," Organometallics 12:870-875, 1993.

Humphries et al., "Investigations into the Mechanism of Activation and Initiation of Ethylene Polymerization by Bis(imino)pyridine Cobalt Catalysts: Synthesis, Structures, and Deuterium Labeling Studies," Organometallics 24:2039-2050, 2005.

Ikariya, "Bifunctional Transition Metal-Based Molecular Catalysts for Asymmetric Syntheses," Top Organomet Chem 37:31-53, 2011 (published online Mar. 12, 2011).

Ingleson et al., "Reducing Power of three-Coordinate Cobalt(I)," Journal of the American Chemical Society 128:4248-4249, 2006 (published online Mar. 14, 2006).

Ingleson et al., "Redox Chemistry of the Triplet Complex (PNP)Co1," Journal of the American Chemical Society 130:4262-4276, 2008 (published online Mar. 11, 2008).

Ingleson et al., "Three-Coordinate Co(I) Provides Access to Unsaturated Dihydrido-Co(III) and Seven-Coordinate Co(V)," Journal of the American Chemical Society 128:1804-1805, 2006 (published online Jan. 24, 2006).

Jacobsen et al., "Hydrogen production using cobalt-based molecular catalysts containing a proton relay in the second coordination sphere," Energy Environ. Sci., 1:167-174, 2008.

Jenkins et al., "A Mechanistic Investigation of the Polymerization of Ethylene Catalyzed by Neutral Ni(II) Complexes Derived from Bulky Anilinotropone Ligands," Journal of the American Chemical Society 126:5827-5842, 2004 (published online Apr. 20, 2004).

Jia et al., "Aminophosphine ligands R2P(CH2)nNH2 and ruthenium hydrogenation catalysts RuCl2(R2P(CH2)nNH2)2," Dalton Transactions 8301-8307, 2009 (published online Aug. 12, 2009).

Johnson et al., "Industrial-Scale Synthesis and Applications of Asymmetric Hydrogenation Catalysts," Acc. Chem. Res. 40(12):1291-1299, 2007 (published online Sep. 6, 2007).

Kanai et al., "Isomerization of 1-Butane Catalyzed by (η6-Arene)NiR2. A Very Active Homogeneous Catalyst System," Journal of the American Chemical Society 108:2019-2023, 1986.

Knijnenburg et al., "Olefin hydrogenation using diimine pyridine complexes of Co and Rh," Journal of Molecular Catalysis A: Chemical 232:151-159, 2005.

Knijnenburg et al., "The Electronic Structure of (Diiminopyridine)cobalt(I) Complexes," Eur. J. Inorg. Chem. 1204-1211, 2004.

(56) References Cited

OTHER PUBLICATIONS

Knowes et al., "Pioneering Perspectives on Asymmetric Hydrogenation," Acc. Chem. Res. 40(12):1236-1239, 2007 (published online Dec. 18, 2007).
Kobayashi et al., "Cobalt-mediated Reduction of C=N Bond. Synthesis of Methyl N-p-Toluenesulfonyl-1-phenylglycinate Catalyzed by Bis(dioximato)cobalt-Quinine Complexes," Chemistry Letters 2031-2034, 1986.
Laird et al., "Selectivity of attack on a Si—C(sp3) sigma bond coordinated to NiII," Inorganica Chimica Acta 374:79-87, 2011 (published online Dec. 30, 2010).
Langer et al., "Efficient Hydrogenation of Ketones Catalyzed by an Iron Pincer Complex," Angew. Chem. Int. Ed. 50:2120-2124, 2011.
Liang et al., "Phosphorus and Olefin Substituent Effects on the Insertion Chemistry of Nickel(II) Hydride Complexes Containing Amido Diphosphine Ligands," Organometallics 27:3082-3093, 2008 (published online May 29, 2008).
Liang et al., "Intermolecular Arene C—H Activation by Nickel(II)," Journal of the American Chemical Society 128:15562-15563, 2006 (published online Nov. 14, 2006).
Liang et al., "Amido Pincer Complexes of Nickel(II): Synthesis, Structure, and Reactivity," Organometallics 25:1399-1411, 2006 (published online Feb. 1, 2006).
Maire et al., "Chiral Rhodium(I) and Iridium(I) Amino-Olefin Complexes: pKa, N—H Bond Dissociation Energy, and Catalytic Transfer Hydrogenation," Organometallics 24:3207-3218, 2005 (published online May 24, 2005).
Marziale et al., "Palladium N(CH2CH2PiPr2)2-Dialkylamides: Synthesis, Structural Characterization, and Reactivity," Inorganic Chemistry 48(8):3699-3709, 2009 (published online Mar. 12, 2009).
Meiners et al., "Square-Planar Iridium(II) and Iridium(III) Amido Complexes Stabilized by a PNP Pincer Ligand," Angew. Chem. Int. Ed. 50:8184-8187, 2011.
Meyer et al., "Iron(II) Complexes for the Efficient Catalytic Asymmetric Transfer Hydrogenation of Ketones," Chem. Eur. J. 15:5605-5610, 2009.
Monfette et al., "Enantiopure C1-Symmetric Bis(imino)pyridine Cobalt Complexes for Asymmetric Alkene Hydrogenation," Journal of the American Chemical Society 134:4561-4564, 2012 (published online Mar. 6, 2012).
Nindakova et al., "Enantioselective Hydrogenation over Chiral Cobalt Complexes with (+)-(1S,2S,5R)-Neomenthyldiphenylphosphine and (−)-(R,R)-2,2-Dimethyl-4,5-bis(diphenylphosphinomethyl)-1,3-dioxolane," Russian Journal of Organic Chemistry 40(7):973-975, 2004.
O'Hagan et al., "Moving Protons with Pendant Amines: Proton Mobility in a Nickel Catalyst for Oxidation of Hydrogen," Journal of the American Chemical Society 133:14301-14312, 2011 (published online May 19, 2011).
Ohgo et al., "Asymmetric Hydrogenation Catalyzed by Bis(Dimethylglyoximato) Cobalt(II)-Achiral Base Complex and Chiral Aminoalcohol Conjugated Systems. An Oxido-Reductase Model with Enantioselectivity," Chemistry Letters 1327-1330, 1974.
Ozerov et al., "Oxidative Addition of N—C and N—H Bonds to Zerovalent Nickel, Palladium, and Platinum," Organometallics 23:5573-5580, 2004 (published on Oct. 9, 2004).
Poli, "Paramagnetic Mono- and Polyhydrides of the Transition Metals," Paramagnetic Hydrides, Chapter 6, 139-188, 2002.
Pregaglia et al., "Catalysis by Phosphine Cobalt Carbonyl Complexes I. Synthesis and Catalytic Properties of (Tributylphosphine)Cobalt (I) Hydride Carbonyl Complexes," Journal of Organometallic Chemistry 30:387-405, 1971.
Radlauer et al., "Dinickel Bisphenoxyiminato Complexes for the Polymerization of Ethylene and α-Olefins," Organometallics 31:2231-2243, 2012 (published online Mar. 8, 2012).
Rakowski et al., "Catalytic Homogeneous Hydrogenation of Arenes. 4. Characterization of the Basic Reaction and the Catalysts," Inorganic Chemistry 15(10):2379-2382, 1976.
Reger et al., "Influence of the size of the phosphine ligand on primary-secondary alkyl isomerization equilibria with (me2NCS2)Pt(PR3)(alkyl) complexes," Journal of Organometallic Chemistry 452:263-270, 1993.
Ren et al., "A Structure-Activity Study of Ni-Catalyzed Alkyl-Alkyl Kumadad Coupling. Improved Catalysts for Coupling of Secondary Alkyl Halides," Journal of the American Chemical Society 133:7084-7095, 2011 (published online Apr. 18, 2011).
Rigo et al., "Nickel(0) Complexes with the Hybrid Bidentate Ligand 1-(Thioethyl)-2-(diphenylphosphino)ethane. Synthesis Nickel Hydride Derivative," Inorganic Chemistry 18(3):860-863, 1979.
Sanders et al., "Oxidation Reactions of Hydridotetrakis(diethoxyphenylphosphine)-cobalt(II) Hexafluorophosphate: Preparation of Cationic Hydrido-cobalt(III) Complexes," J.C.S. Dalton 2340-2342, 1975.
Sanders et al., "Paramagnetic Hydrido-complexes of Cobalt(II)," J.C.S. Dalton 748-749, 1973.
Schunn et al., "Stable Nickel Hydride Complexes," Inorganic Chemistry 9(2):394-395, Feb. 1970.
She et al., "Insertion of Alkynes into Ni—H Bonds: Synthesis of Novel Vinyl Nickel(II) and Dinuclear Vinyl Nickel(II) Complexes Containing a [P,S]-Ligand," Organometallics 26:566-570, 2007 (published online Dec. 24, 2006).
Smith et al., "Reversible Electrocatalytic Production and Oxidation of Hydroen at Low Overpotentials by a Functional Hydrogenase Mimic," Angew. Chem. Int. Ed 51:1-5, 2012.
Trovitch et al., "Functional Group Tolerance and Substrate Scope in Bis(imino)pyridine Iron Catalyzed Alkene Hydrogenation," Organometallics 27:1470-1478, 2008 (published Mar. 13, 2008).
van der Vlugt, "Cooperative Catalysis with First-Row Late Transition Metals," Eur. J. Inorg. Chem. 363-375, 2012.
Vechorkin et al., "Cross-Coupling of Nonactivated Alkyl Halides with Alkynyl Grignard Reagents: A Nickel Pincer Complex as the Catalyst," Angew. Chem. Int. Ed. 50:11777-11781, 2011.
Vechorkin et al., "Functional Group Tolerant Kumada—Corriu—Tamao Coupling of Nonactivated Alkyl Halides with Aryl and Heteroaryl Nucleophiles: Catalysis by a Nickel Pincer Complex Permits the Coupling of Functionalized Grignard Reagents," Journal of the American Chemical Society 131:9756-9766, 2009 (published online Jun. 24, 2009).
Waldron et al., "Asymmetric Homogeneous Hydrogenation Catalyzed by a Cobalt Complex. High Enantiomeric Excess via Statistically Designed Experiments and Mechanistic Studies," Inorganic Chemistry 16(5):1220-1225, 1977.
Wender et al., "Mechanism of the Oxo and Related Reactions. III. Evidence for Homogeneous Hydrogenation," Communications to the Editor 4842-4843, Oct. 1950.
Wender et al., "Chemistry of the Oxo and Related Reactions. II. Hydrogenation," 72:4375-4378, Oct. 1950.
Whitesides et al., "Suppression of Unwanted Heterogeneous Platinum(0)-Catalyzed Reactions by Poisoning with Mercury(0) in Systems Involving Competing Homogeneous Reactions of Soluble Organoplatinum Compounds: Thermal Decomposition of Bis(triethylphosphine)-3,3,4,4,-tetramethylplatinacyclopentane," Organometallics 4:1819-1830, 1985.
W.N.O. et al., "Mechanistic Investigation of the Hydrogenation of Ketones Catalyzed by a Ruthenium(II) Complex Featuring an N-Heterocyclic Carbene with a Tethered Primary Amine Donor: Evidence for an Inner Sphere Mechanism," Organometallics 30:1236-1252, 2011.
W.N.O. et al., "Bifunctional Mechanism with Unconventional Intermediates for the Hydrogenation of Ketones Catalyzed by an Iridium(III) Complex Containing an N-Heterocyclic Carbene with a Primary Amine Donor," Organometallics 31:2152-2165, 2012 (published online Mar. 6, 2012).
Yamamoto et al., "Synthesis and Properties of Hydridodinitrogentris (triphenylphosphine) cobalt(I) and the Related Phosphine-Cobalt Complexes," Journal of the American Chemical Society 93(2):371-380 Jan. 27, 1971.
Zhu et al., "(Py)2Co(CH2SiMe3)2 As an Easily Accessible Source of "CoR2"," Organometallics 29:1897-1908, 2010 (published online Mar. 19, 2010).

\* cited by examiner

CATALYTIC HYDROGENATION USING COMPLEXES OF BASE METALS WITH TRIDENTATE LIGANDS

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The invention relates to catalytic hydrogenation of unsaturated compounds using complexes of base metals with tridentate ligands.

BACKGROUND OF THE INVENTION

Catalytic hydrogenation is used for the production of bio-renewable chemicals, fuels, commodity chemicals, fine chemicals, and pharmaceuticals. Complexes of precious metals (e.g. Rh, Ir, Ru, Pd, or Pt) and ligands are used for catalytic hydrogenation. They exhibit high functional group tolerance, have long lifetimes and high activities, and may be used for hydrogenating carbonyl (C=O) groups, alkene (C=C) groups, alkyne (C≡C) groups, imine (C=N) groups, nitrile (C≡N) groups, and the like. Complexes of the precious metals rhodium, ruthenium, and iridium have been used for asymmetric catalytic hydrogenation. The development of base-metal-containing complexes (e.g. complexes of Mn, Fe, Co, Ni, Cu, and the like) for hydrogenation has lagged behind, perhaps because base metals tend to engage in one-electron or radical chemistry. Several complexes of iron, for example, were reported for catalytic hydrogenation of ketone groups or alkene groups, but the effectiveness of such complexes typically has been restricted to a particular class of substrate, and such complexes are often sensitive to water and also to compounds with oxygen-containing groups and/or nitrogen-containing groups.

Complexes of cobalt may be used for homogeneous hydrogenation of unsaturated compounds. $HCo(CO)_4$, $Co(H)(CO)(P''Bu_3)_3$, and related cobalt(I) complexes, for example, are used for the catalytic hydrogenation of alkenes and arenes at temperatures greater than 120° C. and pressures greater than 30 atm of hydrogen ("$H_2$"). Complexes of cobalt with diiminopyridine ligands as well as the dinitrogen complex $Co(H)(N_2)(PPh_3)_3$ are used for the catalytic hydrogenation of olefins at room temperature, and an asymmetric hydrogenation of substituted styrenes was recently developed. The cobalt(I) dihydrogen complex $[(P(CH_2CH_2PPh_2)_3)Co(H_2)]BPh_4$ was used for the catalytic hydrogenation of carbon dioxide ($CO_2$) and bicarbonates to formic acid derivatives.

Reports are scarce for catalytic hydrogenation of aldehydes and ketones using complexes of cobalt. Aldehyde hydrogenation was reported as a side reaction in the catalytic hydroformylation of olefins at 185° C. with $Co_2(CO)_8$ and 300 atm of synthesis gas. The catalytic hydrogenation of aldehydes using the cobalt complex $Co(II)(CO)(P''Bu_3)_3$ with 30 atm $H_2$ has been reported, but reaction was complicated by a competing aldehyde decarbonylation reaction. A complex of cobalt and dioxime ligand has been used for the catalytic asymmetric hydrogenation of benzil, but the substrate scope was limited to 1,2-dicarbonyl compounds.

Nearly all prior examples of catalytic hydrogenation with complexes of cobalt have employed cobalt(I), i.e. cobalt in the +1 oxidation state, and most of these examples have been limited in substrate scope.

There are some examples of catalytic hydrogenation with complexes of nickel. A complex of nickel with a diphosphine-borane ligand was used for styrene hydrogenation at room temperature. The hydrogen activation mechanism was suggested to involve a cooperative metal-ligand interaction in which a nickel(0) complex accepts a proton and the boron on the ligand serves as a hydride acceptor.

Caulton et al. reported a complex of nickel of the formula $[(PNP')Ni]BAr^F_4$ ($PNP'=^-N(SiMe_2CH_2P(^tBu)_2)_2$) and proposed that it cleaved $H_2$ heterolytically through a pathway having $Ni^{IV}$ dihydride character. The PNP ligand is sometimes referred to in the art as a "pincer" ligand. This unusual example of $H_2$ activation may involve an interaction between the nickel and the nitrogen of the pincer ligand shown in Scheme 1.

Scheme 1

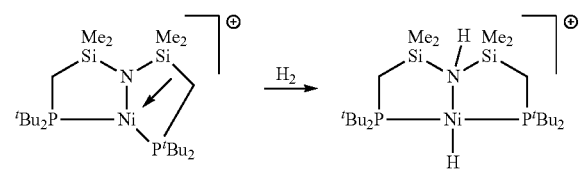

These types of interactions between the metal and ligand might also be involved in catalytic hydrogenation of polar multiple bonds using complexes of precious metals.

SUMMARY OF THE INVENTION

An aspect of the invention relates to a composition of the formula

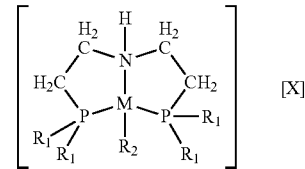

wherein $R_1$ is selected independently from cycloalkyl, alkyl, substituted alkyl, phenyl, or substituted phenyl;

wherein $R_2$ is selected from $-CH_2Si(CH_3)_3$, H, alkyl, substituted alkyl, phenyl, substituted phenyl, amido, alkoxide;

wherein M is cobalt or nickel; and wherein X is a counterion.

Another aspect of the invention relates to a composition of the formula

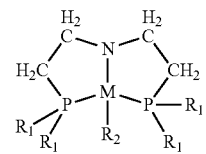

wherein $R_1$ is selected independently from cycloalkyl (e.g. cyclohexyl, adamantyl), alkyl, substituted alkyl, phenyl, or substituted phenyl;

wherein $R_2$ is —$CH_2Si(CH_3)_3$, H, alkyl, substituted alkyl, phenyl, substituted phenyl, alkoxide or amido; and wherein M is cobalt or nickel.

Another aspect of the invention relates to a process for hydrogenation. The process involves combining a composition of the formula

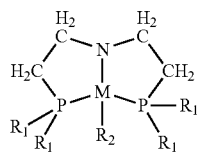

or of the formula

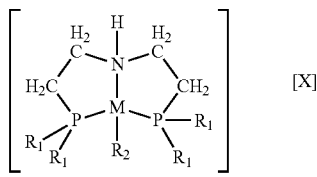

wherein $R_1$ is selected independently from cycloalkyl, alkyl, substituted alkyl, phenyl, or substituted phenyl;

wherein $R_2$ is —$CH_2Si(CH_3)_3$, hydrogen, or alkyl, substituted alkyl, phenyl, substituted phenyl, alkoxide, or amido;

wherein M is cobalt or nickel, and wherein X is a counterion, with hydrogen and an unsaturated compound under conditions effective for hydrogenation of the unsaturated compound.

DETAILED DESCRIPTION

Embodiment complexes of cobalt and of nickel were synthesized and used for catalytic homogeneous hydrogenation of unsaturated compounds. Embodiment cobalt complexes include cobalt in the +2 oxidation state (i.e. cobalt (II)) and the tridentate ligands bis[2-(dialkylphosphino)-ethyl]amine ($HN(CH_2CH_2P(R)_2)_2$ ("PNHP$^R$", where R=cyclohexyl, alkyl, substituted alkyl, phenyl, or substituted phenyl). These bulky ligands are sometimes referred to in the art as "pincer" ligands. The hydrogenation reactions using these embodiment cobalt complexes take place under relatively mild conditions. Embodiment complexes of nickel with the PNHP$^R$ ligand were also prepared and used for catalytic homogeneous hydrogenation of unsaturated compounds. Some embodiment complexes that fall within the scope of this invention have the formula

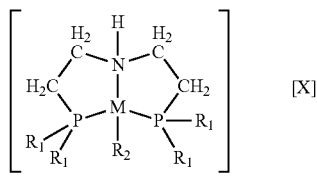

wherein $R_1$ is selected independently from cycloalkyl (e.g. cyclohexyl, adamantyl), alkyl, substituted alkyl, phenyl, or substituted phenyl;

wherein $R_2$ is —$CH_2Si(CH_3)_3$, H, alkyl, substituted alkyl, phenyl, substituted phenyl, alkoxide, or amido;

wherein M is cobalt or nickel; and wherein X is a counterion. Some non-limiting examples of counterions X include tetraphenylborate, hexafluorophosphate, $B(C_6F_5)_4$, or $B(3,5-(CF_3)_2C_6H_3)_4$. Other embodiment complexes that also fall within the scope of this invention have the formula

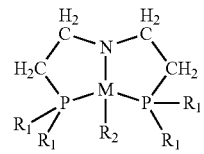

wherein $R_1$ is selected independently from cycloalkyl (e.g. cyclohexyl, adamantyl), alkyl, substituted alkyl, phenyl, or substituted phenyl;

wherein $R_2$ is —$CH_2Si(CH_3)_3$, H, alkyl, substituted alkyl, phenyl, substituted phenyl, alkoxide, or amido; and wherein M is cobalt or nickel.

The embodiment cobalt complexes will be described first.

Unless specified otherwise, all reactions were carried out under a dry argon atmosphere using standard glove-box and Schlenk techniques. Deuterated solvents were purchased from CAMBRIDGE ISOTOPE LABORATORIES. Benzene-$d_6$ and THF-$d_8$ were dried over Na metal, and $CD_2Cl_2$ was dried over $CaH_2$. Anhydrous grade THF, pentane, benzene, toluene, and diethyl ether were obtained from ALDRICH or ACROS and stored over 4 Å molecular sieves. $^1H$, $^{13}C$, and $^{31}P$ NMR spectra were obtained at room temperature on a BRUKER AV400 MHz spectrometer, with chemical shifts (δ) referenced to the residual solvent signal ($^1H$ and $^{13}C$) or referenced externally to $H_3PO_4$ (0 ppm). GC-MS analysis was obtained using a HEWLETT PACKARD 6890 GC system equipped with a HEWLETT PACKARD 5973 mass selective detector. UV-vis spectra were obtained on an AGILENT 8453 UV-visible spectrophotometer equipped with a PELTIER thermostatted single cell holder. IR spectra were obtained on a PERKIN-ELMER SPECTRUM ONE instrument. Elemental analyses were performed by ATLANTIC MICROLAB of Norcross, Ga. Bis[2-(dicyclohexylphosphino)ethyl]amine (abbreviated as PNHP$^{Cy}$) was prepared by a previously reported procedure or purchased from STREM CHEMICAL. Cyclohexene-$d_{10}$ was purchased from C/D/N ISOTOPES, INC. The complexes $(pyr)_2Co(CH_2SiMe_3)_2$ and $H[BAr^F_4].(Et_2O)_2$ were prepared according to previously published procedures. BArF$^4$ is the abbreviation for the bis-3,5-trifluoromethyltetraphenylborate anion. $Et_2O$ is the abbreviation for diethyl ether. "Me" is the abbreviation for methyl. "Pyr" is the abbreviation for pyridine.

Reaction of PNHP$^{Cy}$ with $(pyr)_2Co(CH_2SiMe_3)_2$ afforded the paramagnetic cobalt(II) complex (PNP$^{Cy}$)Co ($CH_2SiMe_3$) (1) as dark yellow crystals in 82% isolated yield. In the solid state, complex 1 has a square planar geometry. In solution, complex 1 exhibits a magnetic moment that is consistent with a square planar low-spin $d^7$ configuration ($\mu_{eff}$=2.2$\mu_B$). In the solution state, the magnetic moment of complex 1 has a value close to 2.1$\mu_B$, which is the value reported for $(N(SiMe_2CH_2PPh_2)_2)Co(CH_2SiMe_3)$, which also has a square planar geometry. This procedure was effective for the synthesis of complexes of the composition $(PNP^R)Co(CH_2SiMe_3)$ where R=cyclohexyl, alkyl, substituted alkyl, phenyl, or substituted phenyl.

Addition of one equivalent of the known acid $H[BAr^F_4].(Et_2O)_2$ ($BAr^F_4$=B(3,5-$(CF_3)_2C_6H_3)_4$) to a THF-$d_8$ solution of complex 1 resulted in paramagnetic complex $[(PNHP^{Cy})Co(CH_2SiMe_3)]BAr^F_4$ (2). The structural formulas of complexes 1 and 2 are shown below (Me=methyl).

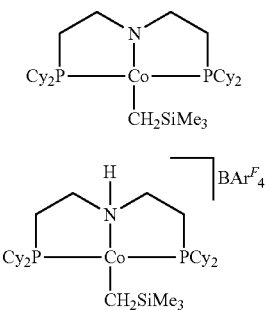

Complex 2 was detected by $^1H$ NMR spectroscopy in 90% yield (integration against an internal standard). Complex 2 was isolated in 85% yield and characterized by NMR and IR spectroscopy, X-ray crystallography, and elemental analysis. The $^1H$ NMR spectrum of complex 2 showed a broad peak at −20.88 ppm corresponding to the $Si(CH_3)_3$ protons on the alkyl ligand, and the IR spectrum of 2 showed an N—H stretch at 3147 cm$^{-1}$.

Complexes 1 and 2 were used for the catalytic hydrogenation of styrene. Hydrogenation was slow using 2 mol % of complex 1, with only about 2% conversion of styrene to ethylbenzene observed after 24 hours at 60° C. under 1 atmosphere of hydrogen ("$H_2$"). Hydrogenation of styrene was faster using complex 2; complete conversion (50 turnovers) was observed for the hydrogenation of styrene to ethylbenzene within 2 hours at room temperature under just 1 atm hydrogen using 2 mol % of complex 2, which was generated in situ from complex 1 and $H[BAr^F_4].(Et_2O)_2$) in THF solution. Results were identical when an isolated sample of complex 2 was used.

The hydrogenation of styrene using complex 2 was not affected by the addition of excess Hg metal. This observation is consistent with the presence of an active homogeneous catalyst. With a lower catalyst loading (0.05 mol % complex 1 and 0.05 mol % $H[BAr^F_4].(Et_2O)_2$), 1100 turnovers were observed after 24 hours at room temperature for the hydrogenation of styrene (1 atm $H_2$). A variety of substrates were hydrogenated using complex 2 generated in situ by combining complex 1 (2 mol %) and $H[BAr^F_4].(Et_2O)_2$ (2 mol %) in THF (see Equation 1 below).

(Equation 1)

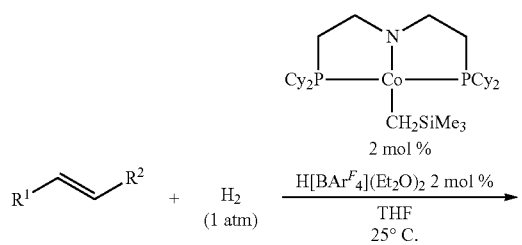

In the above equation, $R^1$ and $R^2$ are independently selected from hydrogen, alkyl, aryl, substituted alkyl, and substituted aryl groups. The hydrogenation reaction conditions included a substrate concentration of 0.5 millimolar in tetrahydrofuran (THF) solvent and 1 atmosphere $H_2$ at 25° C. Results of the hydrogenation reactions are summarized in Table 1 below.

TABLE 1

| Entry | substrate | product | time (h) | yield (%) |
|---|---|---|---|---|
| 1 | styrene | ethylbenzene | 24 | 100 |
| 2 | 4-fluorostyrene | 4-fluoroethylbenzene | 24 | 100 |
| 3 | 4-methoxystyrene | 4-methoxyethylbenzene | 24 | 99 |
| 4 | trans-β-methylstyrene | propylbenzene | 24 | 100 |
| 5 | α-methylstyrene | isopropylbenzene | 24 | 99 |
| 6 | allylbenzene | propylbenzene | 24 | 100 |
| 7 | 1-octene | octane | 24 | 99 |
| 8 | internal octene | octane | 24 | 100 |
| 9 | cis-cyclooctene | cyclooctane | 24 | 100 |
| 10 | norbornene | norbornane | 24 | 100 |
| 11 | 4-isopropenyl-1-methylcyclohexene | 4-isopropyl-1-methylcyclohexene | 40 | 80 |

TABLE 1-continued

| Entry | substrate | product | time (h) | yield (%) |
|---|---|---|---|---|
| 12 | (structure) | (structure) | 42 | 99 |

The yields of the hydrogenated products were determined by gas chromatography (GC). Hydrogenation of terminal alkenes such as 1-octene and α-methylstyrene proceeded readily within 24 hours at room temperature with excellent yields (see Table 1, entries 5-7). Internal alkenes trans-2-octene, cis-cyclooctene, and norbornylene were also hydrogenated at room temperature (see Table 1, entries 8-10). Hydrogenation of (R)-(+)-limonene occurred selectively at the terminal position; the internal tri-substituted C=C bond was not hydrogenated (see Table 1, entry 11). At room temperature, hydrogenation of (+)-dihydrocarvone occurred only at the C=C bond, affording 5-isopropyl-2-methylcyclohexanone in 99% yield (see Table 1, entry 12).

Complex 2 generated in situ from complex 1 (2 mol %) and $H[BAr^F_4].(Et_2O)_2$ (2 mol %) was also used for hydrogenating aldehydes, ketones, and imines (Equation 2 below).

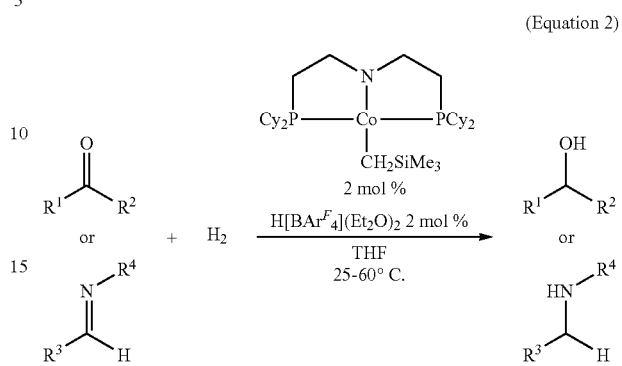

(Equation 2)

In the above equation, $R^1$, $R^2$, $R^3$, and $R^4$ are independently selected from hydrogen, alkyl, aryl, substituted alkyl, and substituted aryl groups. The hydrogenations of the aldehydes and ketones took place under mild conditions, which was unexpected in view of the mild reaction conditions and scarcity of reported cobalt complexes that hydrogenate aldehydes and ketones. The results for the aldehyde, ketone, and imine hydrogenations are summarized in Table 2.

TABLE 2[a]

| Entry | substrate | product | time (h) | isolated yield (%) (NMR yield) |
|---|---|---|---|---|
| 1 | (acetophenone) | (1-phenylethanol) | 24 | 89 (98) |
| 2[c] | (2'-bromoacetophenone) | (1-(2-bromophenyl)ethanol) | 43 | 86 (94) |
| 3[c] | (3'-methoxyacetophenone) | (1-(3-methoxyphenyl)ethanol) | 24 | 92 (98) |
| 4[c] | (2,2,2-trifluoroacetophenone) | (2,2,2-trifluoro-1-phenylethanol) | 48 | 91 (99) |
| 5[c] | (2-indanone) | (2-indanol) | 48 | 97 (99) |

TABLE 2[a]-continued

| Entry | substrate | product | time (h) | isolated yield (%) (NMR yield) |
|---|---|---|---|---|
| 6[c] | pentan-2-one | pentan-2-ol | 24 | 100[f] |
| 7[d] | hex-5-en-2-one | hexan-2-ol | 65 | 99[f] |
| 8 | benzaldehyde | benzyl alcohol | 24 | 86 (92) |
| 9 | 2-bromobenzaldehyde | 2-bromobenzyl alcohol | 24 | 96 (100) |
| 10[b] | 4-methoxybenzaldehyde | 4-methoxybenzyl alcohol | 24 | 92 (98) |
| 11[b] | 2-methoxybenzaldehyde | 2-methoxybenzyl alcohol | 24 | 91 (99) |
| 12[e] | octanal | octan-1-ol | 64 | 92 (100) |
| 13[e] | N-benzylidenebenzylamine | dibenzylamine | 42 | 84 (89) |
| 14[e] | N-benzylidenemethylamine | N-methylbenzylamine | 72 | 88 (98) |
| 15[e] | N-benzylideneaniline | N-benzylaniline | 48 | 65 (70) |

[a] Conditions: substrate 0.5 mmol in THF (2 mL), 1 atm $H_2$, 25° C.
[b] Reactions run at 50° C.
[c] Reactions run at 60° C.
[d] Reactions run at 25° C. under 4 atm $H_2$ pressure.
[e] Reactions run at 60° C. under 4 atm $H_2$ pressure.
[f] yields were determined by GC-MS.

As Table 2 shows, acetophenone (entry 1) was hydrogenated using complex 2 in nearly quantitative yield within 24 hours at room temperature 1 atm of hydrogen. Several substituted acetophenone derivatives were hydrogenated at 60° C. (1 atm $H_2$), including 2-bromoacetophenone, 3-methoxyacetophenone, and α-trifluoromethylacetophenone (86-92% isolated yields, Table 2, entries 2-4). Aliphatic ketones 2-hexanone and 2-indanone were hydrogenated in high yields when the reaction was run at 60° C. (1 atm $H_2$) for 24 hours and 48 hours, respectively (Table 2, entries 5-6). Aldehydes were also hydrogenated by in situ-generated complex 2 (2 mol %). Benzaldehyde and the substituted benzaldehydes 2-bromobenzaldehyde, 2-methoxybenzaldehyde, and 4-methoxybenzaldehyde were hydrogenated to the corresponding alcohols in excellent yields (86-96% isolated yields) within 24 hours under 1 atm of hydrogen (Table 2, entries 8-11). The unsubstituted aliphatic aldehyde 1-octanal was hydrogenated more slowly, affording 1-octanol in 92% isolated yield after 64 hours at 60° C. under 4 atm $H_2$ (Table 2, entry 12). The effectiveness of cobalt complex 2 in hydrogenation reactions of aldehydes stands in contrast to the effectiveness of the known iron complex $(PNP^{tBu})Fe(H)(CO)(Br)$ ($PNP^{tBu}$=2,6-bis(di-tert-butylphosphinomethyl)pyridine). The iron complex was reported to be effective for the hydrogenation of a number of ketones; low conversion (39%) was reported for hydrogenation of benzaldehyde.

Imines were hydrogenated using in situ-generated complex 2. Hydrogenation of N-benzylidene benzylamine proceeded under 4 atm $H_2$ at 60° C. to afford dibenzylamine in 84% isolated yield using 2 mol % of complex 2 (Table 2, entry 13). N-Benzylidenemethylamine and N-benzylideneaniline were also hydrogenated by the cobalt catalyst, affording N-benzyl methyl amine and N-benzylaniline in good yields (Table 2, entries 14 and 15). Previous examples of cobalt-catalyzed imine hydrogenation are scarce.

Given the broad substrate scope demonstrated, we performed further experiments to assess the functional group tolerance of the cobalt catalytic system. Table 3 summarizes the results of some experiments for assessing the functional group tolerance of complex 2. Hydrogenation of the alkene moiety in tert-butyl-3-butenoate was unaffected by the presence of the ester, proceeding in high yield (99% GC yield) using in situ generated 2 (2 mol %) after 24 h at room temperature (1 atm $H_2$, Table 3, entry 1). Surprisingly, complex 2 catalyzed the hydrogenation of 4-pentenoic acid to afford pentanoic acid (82% isolated yield), although somewhat more forcing conditions were required (1 atm $H_2$, 60° C., 24 h, Table 3, entry 2). 4-Penten-1-ol was also hydrogenated in quantitative GC yield within 24 h at room temperature (1 atm $H_2$, Table 3, entry 3). The cobalt catalyst was also active in the presence of a secondary amine, hydrogenating N-methyl-4-piperidone to N-methyl-4-piperidinol in 66% GC yield.

TABLE 3

| Entry | substrate | product | time (h) | yield (%) |
|---|---|---|---|---|
| 1 | (alkene ester) | (alkane ester) | 24 | 99 |
| 2[a] | (4-pentenoic acid) | (pentanoic acid) | 24 | 82 (99) |

TABLE 3-continued

| Entry | substrate | product | time (h) | yield (%) |
|---|---|---|---|---|
| 3 | (4-penten-1-ol) | (1-pentanol) | 24 | 99 |
| 4[a] | N-methyl-4-piperidone | N-methyl-4-piperidinol | 65 | 66 |
| 5 | styrene + $H_2O$ (10 mol %) | ethylbenzene + $H_2O$ (10 mol %) | 24 | 99 |

As water can be an impurity in reagents and solvents, the activity of complex 2 (2 mol %) was tested in a hydrogenation reaction of styrene in the presence of 10 mol % water added to the reaction mixture. Although the hydrogenation reaction was somewhat inhibited by the water, hydrogenation proceeded to generate ethylbenzene in 99% yield after 24 hours at room temperature. The ability of the cobalt complex 2 to tolerate other functional groups and added water is remarkable to us because this behavior appears more like the behavior of complexes of precious metals than the behavior of complexes of base metals in catalytic hydrogenation reactions.

Additional experiments were performed to gain insight into possible catalytic reaction mechanisms. One atmosphere of hydrogen was added to a THF-$d_8$ solution of paramagnetic cobalt(II) alkyl complex 2 and the mixture was monitored by $^1H$ NMR spectroscopy. Within 1 hour at room temperature, $^1$NMR signals corresponding to complex 2 disappeared from the $^1H$ NMR spectrum while a new signal at 0 ppm appeared which corresponded to tetramethylsilane (TMS). Although the solution had a yellow color, which might be interpreted as corresponding to the presence of a homogeneous cobalt complex, no signals attributable to such a complex were observed in the $^1H$ NMR spectrum of the solution. The magnetic moment ($\mu_{eff}$) of the solution was approximately 2.7$\mu_B$, measured using the Evans method. This value is consistent with a paramagnetic material.

Other experiments suggested that a cobalt(II) hydride complex 3 may have been formed upon the reaction of cobalt(II) alkyl complex 2 with hydrogen. To test this theory, complex 2 was treated with hydrogen (1 atm) in THF-$d_8$ solution for 3 hours, affording tetramethylsilane and cobalt product(s). Subsequent addition of $CHCl_3$ (2 equiv) resulted in an immediate color change from yellow to red, and the production of $CH_2Cl_2$ (as determined by $^1H$ NMR spectroscopy). The cobalt product of this reaction was isolated and identified as the cobalt(II) chloride complex $[(PNHP^{Cy})Co(Cl)]BAr^F_4$ (4) by X-ray crystallography, IR spectroscopy, and elemental analysis. The formation of chloride complex 4 upon trapping with $CHCl_3$ implies that the hydride complex $[(PNHP^{Cy})Co(H)]BAr^F_4$ (3) was formed upon the reaction of 2 with hydrogen (see Equation 3 below).

Equation 3

(a) 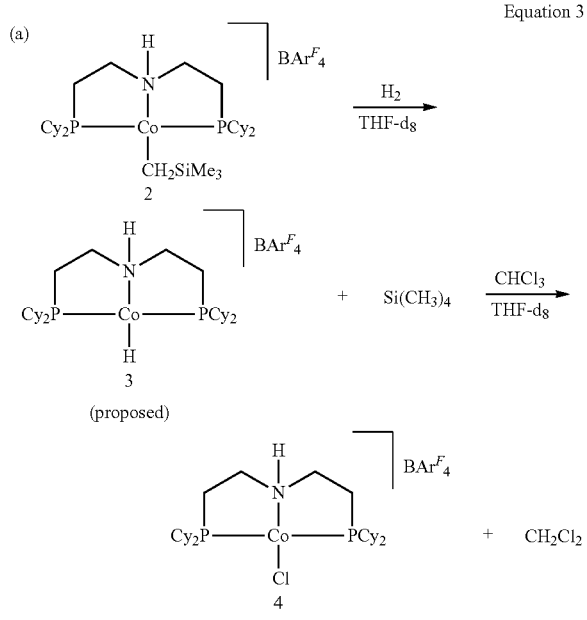

Solutions containing complex 3 catalyzed alkene isomerization rapidly at room temperature. When 1-octene (200 equiv) was added to a degassed THF-d solution containing complex 3, complete isomerization at room temperature occurred within 20 minutes to afford a mixture of internal octenes.

Metal-hydride and π-allyl mechanisms had been commonly proposed for transition-metal mediated olefin isomerization. In a metal-hydride catalyzed pathway, olefin isomerization occurs via olefin insertion into the M-H bond, followed by β-hydride elimination. In the π-allyl mechanism, isomerization occurs by coordination of the olefin to an open site at the metal, C—H activation to generate a π-allyl complex, followed by reductive elimination. Olefin dissociation then regenerates the open site at the metal. We performed a cross-over experiment to distinguish between these two pathways for complex 3 (see Equation 4 below). In Equation 4, "d" refers to deuterium and "h" refers to hydrogen. Thus, cyclohexene-$d_{10}$ refers to a fully deuterated cyclohexene molecule.

Equation 4

(b) 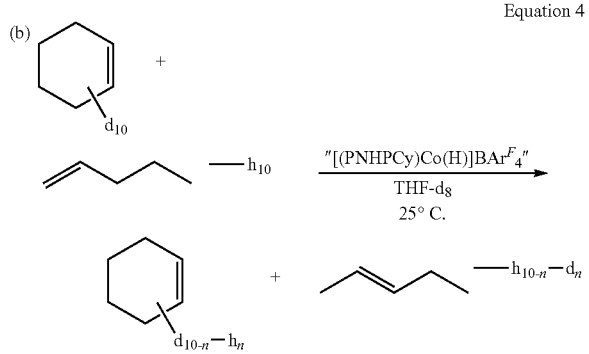

Hydrogen ($H_2$) was added to a mixture of complex 1 and $H[BAr^F_4] \cdot (Et_2O)_2$ in THF-d and allowed to react at room temperature for 1 hour. The hydrogen was removed, and then a 1:1 mixture of cyclohexene-$d_{10}$ and 1-pentene was added. Within 30 minutes at room temperature, isomerization of the 1-pentene to 2-pentene was observed by $^1H$ NMR spectroscopy. In addition, deuterium from the cyclohexene-$d_{10}$ was scrambled into the 2-pentene and resonances corresponding to cyclohexene-$d_{10-n}h_n$ grew into the NMR spectrum, consistent with a pathway for isomerization involving a discreet metal-hydride intermediate. No deuterium exchange would be expected for the π-allyl mechanism.

Few examples of isolable cobalt(II) hydride complexes have been reported, and little is known about their reactivity. Cationic cobalt(II) hydride complexes $[Co(H)(L)_4]^+$ (L=P(OEt)$_2$Ph, P(OPh)$_3$) have been prepared by oxidation of their neutral cobalt(I) analogues. Hydride complex [(triphos)Co(PEt$_3$)H]BPh$_4$ (triphos=CH$_3$C(CH$_2$PPh$_2$)$_3$) has been structurally characterized but only limited reactivity studies have been performed with it. The trapping and crossover experiments presented above suggest the involvement of the cobalt(II) hydride complex $[(PNHP^{Cy})Co(H)]BAr^F_4$ in the hydrogenation reactions.

Without wishing to be bound by any theory or explanation, we propose a catalytic cycle in Scheme 2 below for the observed catalytic hydrogenation using complexes of cobalt and PNHP$^{Cy}$.

Scheme 2

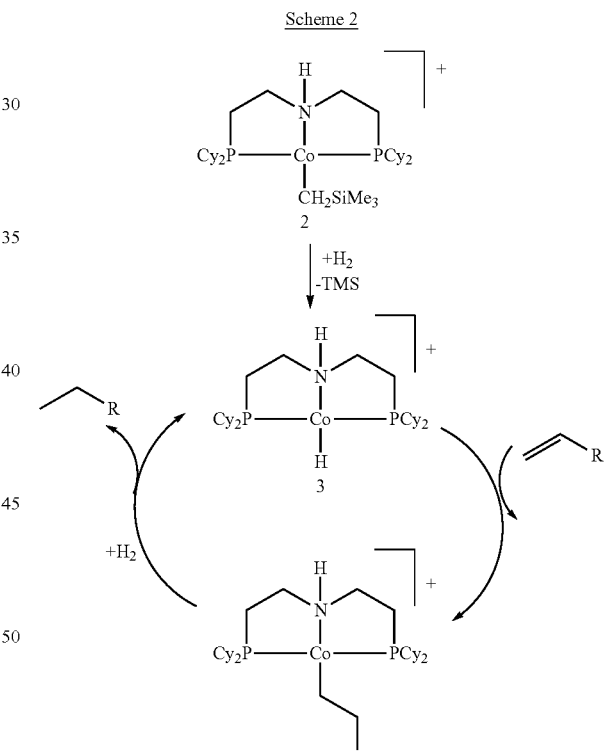

As Scheme 2 shows, hydrogenolysis of the cobalt(II) complex 2 generates cobalt(II) complex 3 and tetramethylsilane. Alkene insertion into the Co—H bond would afford a cobalt(II) alkyl intermediate, which could then react further with hydrogen to release product and turnover the catalyst.

Another possible explanation is that a small amount of a highly active cobalt(I) hydride complex is formed instead. We have been unable to independently prepare such a complex.

Details related to the synthesis of several non-limiting embodiments of complexes of cobalt and PNP$^{Cy}$, PNHP$^{Cy}$, as well as several non-limiting hydrogenation reactions, are provided in the EXAMPLES below.

Examples with Complexes of Cobalt

Synthesis of $(PNP^{Cy})Co(CH_2SiMe_3)$ (1). In a small vial, $PNHP^{Cy}$ (71.0 milligrams ("mg"), 0.153 millimoles ("mmol")) and $(pyridine)_2Co(CH_2SiMe_3)_2$ (61.0 mg, 0.156 mmol) were dissolved in toluene (2 mL) to form a dark green solution. After standing for 20 minutes, the color changed from dark green to yellow-brown. The solvent was removed under vacuum. The residue was dissolved in diethylether (1 milliliter ("mL") and the resulting solution was cooled to −20° C. overnight, which afforded yellow-brown crystals of complex 1. The supernatant was removed by pipette and the crystals were dried under vacuum. Yield: 78 mg (82%). $^1$H NMR (400 MHz, THF-$d_8$) δ 6.55 (br, 2H), 3.38 (br, 8H), 2.69 (br, 8H), 2.00 (br, 6H), 1.62 (br, 4H), 1.29 (br, 6H), 1.12 (br, 6H), 0.89 (br, 6H), 0.22 (br, 6H), −5.26 (br, 9H, Si(CH$_3$)$_3$). UV-vis: 286 nm (ϵ=1580 M$^{-1}$ cm$^{-1}$), 348 nm (ϵ=1060 M$^{-1}$ cm$^{-1}$), 428 nm (ϵ=380 M$^{-1}$ cm$^{-1}$). $\mu_{eff}$=2.2$\mu_B$. Anal. Calcd for $C_{32}H_{63}CoNP_2Si$: C, 62.92; H, 10.40; N, 2.29. Found: C, 62.77; H, 10.24; N, 2.13.

Synthesis of $(PNP^{Ph})Co(CH_2SiMe_3)$

In a vial, bis(diphenylphosphino)ethylamine (74 mg, 0.18 mmol) was dissolved in toluene (2 mL). To the toluene solution was added a solution of $(pyr)_2Co(CH_2SiMe_3)_2$ (62 mg, 0.16 mmol) in toluene (2 mL). The reaction mixture turned a red color. The toluene was removed under vacuum, and the red residue was dissolved in diethyl ether (3 mL), and filtered through a plug of celite. The solvent was removed under vacuum, affording a dark red oil. Yield: 64 mg (68%). $^1$H NMR (400 MHz, benzene-$d_6$) δ 8.80 (br), 7.50 (br), 7.13 (br), 6.28 (br), −4.54 (br).

Synthesis of $(PNP^{Ad})Co(CH_2SiMe_3)$

In a small vial, $(pyr)_2Co(CH_2SiMe_3)_2$ (44 mg, 0.11 mmol) and bis(diadamantylphosphino)ethylamine (75 mg, 0.11 mmol) were combined in toluene (1 mL). The solution was allowed to stand at room temperature for 3 hours, during which time the color changed from green to an orange-brown. The solvent was removed under vacuum, and then diethyl ether (1 mL) was added to the orange-brown solid. The suspension was cooled to −20° C. overnight. The supernatant was removed by pipette, and the orange solid dried under vacuum. Yield: 74 mg (81%). $^1$H NMR (400 MHz, THF-$d_8$) δ 6.05 (br), 2.33 (br), 1.99 (br), 1.86 (br), 1.12 (br), −5.73 (br).

Synthesis of $(PNP^{iPr})Co(CH_2SiMe_3)$

In a vial, bis(diisopropylphophino)ethylamine (66 mg, 0.21 mmol) and $(pyr)_2Co(CH_2SiMe_3)_2$ (84 mg, 0.21 mmol) were dissolved in toluene (4 mL). The solution turned a yellow-brown color. The reaction mixture was allowed to stand at room temperature for 10 minutes, and then the solvent removed under vacuum, affording a yellow-brown oil. Yield: 86 mg (88%). $^1$H NMR (400 MHz, benzene-$d_6$) δ 1.98 (br), 0.63 (br), −4.91 (br).

Synthesis of $[(PNHP^{Cy})Co(CH_2SiMe_3)]BAr^F_4$ (2)

In a small vial, complex 1 (6.1 mg, 10 micromoles ("μmol") and $H[BAr^F_4].(Et_2O)_2$ (10.1 mg, 10 μmol) were dissolved in diethyl ether (0.5 mL). The resulting solution was layered carefully with pentane (1.0 mL) and the vial was sealed and then cooled to −25° C. for three days, during which time yellow plates formed. The supernatant was removed by pipette, and then the crystals were washed with pentane (1 mL) and dried under vacuum. Yield: 12.5 mg (85%). $^1$H NMR (400 MHz, THF-$d_8$) δ 16.16 (br, 2H, $PNHP^{Cy}$), 15.43 (br, 2H, $PNHP^{Cy}$), 7.72 (s, 8H, $BAr^F_4$), 7.51 (s, 4H, $BAr^F_4$), 6.06 (br, 2H, $PNHP^{Cy}$), 5.72 (br, 2H, $PNHP^{Cy}$), 4.54 (br, 2H, $PNHP^{Cy}$), 4.09 (br, 2H, $PNHP^{Cy}$), 3.07 (br, 2H, $PNHP^{Cy}$), 2.69 (br, 2H, $PNHP^{Cy}$), 1.54 (br, 2H, $PNHP^{Cy}$), 1.30 (br, 6H, $PNHP^{Cy}$), −0.59 (br, 2H, $PNHP^{Cy}$), −1.64 (br, 2H, $PNHP^{Cy}$), −20.88 (s, 9H, Si(CH$_3$)$_3$). UV-vis: 354 nm (ϵ=2500 M$^{-1}$ cm$^{-1}$), 444 nm (ϵ=310 M$^{-1}$ cm$^{-1}$). $\mu_{eff}$=2.8$\mu_B$. IR (thin film): $v_{N-H}$=3147 cm$^{-1}$. Anal. Calcd for $C_{64}H_{76}BCoF_{24}NP_2Si$: C, 52.11; H, 5.19; N, 0.95. Found: C, 52.13; H, 5.34; N, 0.94.

Synthesis of $[(PNHP^{Cy})Co(Cl)]BAr^F_4$ (4)

In an NMR tube equipped with a rescalable TEFLON stopper, complex 1 (4.4 mg, 7.2 μmol) and $H[BAr^F_4].(Et_2O)_2$ (7.3 mg, 7.2 mol) were dissolved in THF-$d_8$ (0.4 mL). An $^1$H NMR spectrum of the resulting solution revealed formation of complex 2. The solution was subjected to one cycle of freeze-pump-thaw, and then H$_2$ (1 atm) was added. A $^1$H NMR spectrum of the solution three days later revealed that the signals corresponding to complex 2 had disappeared and a new signal at 0 ppm had appeared (corresponding to tetramethylsilane). CHCl$_3$ (1 μL, 0.013 mmol) was added, resulting in an immediate color change from yellow to red. Examination of the $^1$H NMR spectrum revealed formation of CH$_2$Cl$_2$. Following an analogous procedure on a larger scale (10 μmol) allowed for isolation of complex 4 as red blocks by crystallization (layering a toluene/diethyl ether solution with pentane and cooling to −25° C.). The supernatant was removed by pipette, and the red crystals were washed with pentane and dried under vacuum. Yield: 11.0 mg (77%). $^1$H NMR (400 MHz, THF-$d_8$). UV-vis: 410 nm (s=510 M$^{-1}$ cm$^{-1}$), 510 nm (ϵ=350 M$^{-1}$ cm$^{-1}$), 705 nm (ϵ=110 M$^{-1}$ cm$^{-1}$). $\mu_{eff}$=2.4$\mu_B$. IR (thin film): $v_{N-H}$=3104 cm$^{-1}$. Anal. Calcd for $C_{60}H_{65}BClCoF_{24}NP_2$: C, 50.63; H, 4.60; N, 0.98. Found: C, 49.82; H, 4.63; N, 1.09.

General Procedure for C═C Bond Hydrogenation Reactions

In a typical experiment, complex 1 (6.1 mg, 10 μmol) and $H[BAr^F_4].(Et_2O)_2$ (10.1 mg, 10 μmol) were dissolved in tetrahydrofuran ("THF", 2.0 mL) in a 100 mL thick-walled glass vessel equipped with a TEFLON stopcock and a stir bar. The substrate (0.5 mmol) to be hydrogenated was added and then hexamethylbenzene (ca. 32 mg, 0.2 mmol) was added as an internal standard. The reaction vessel was degassed by freeze-pump-thaw, 1 atm of hydrogen gas was admitted, and the vessel was sealed. The resulting solution was stirred at 25° C. for the indicated reaction time. At the end of the reaction time, the reaction vessel was opened under air, the reaction mixture was diluted with dichloromethane, and the yield was determined by GC analysis (integration against the internal standard). Product identities were verified by GC-MS analysis and comparison to authentic samples.

General Procedure for the C═O and C═N Bond Hydrogenation Reactions

In a typical experiment, complex 1 (6.1 mg, 10 μmol) and $H[BAr^F_4].(Et_2O)_2$ (10.1 mg, 10 μmol) were dissolved in THF (2.0 mL) in a 100 mL thick-walled glass vessel equipped with a TEFLON stopcock and a stir bar. The substrate (0.5 mmol) to be hydrogenated was then added. The vessel was degassed by freeze-pump-thaw and then hydrogen (1 or 4 atm) was added. The resulting solution was stirred at the desired temperature (25-60° C.) for the indicated reaction time. At the end of the reaction, the solvent was evaporated and the residue was passed through silica gel in a pipette. The solvent was removed under vacuum and the $^1$H NMR spectrum of the crude product mixture was recorded in $CDCl_3$. Hydrogenation products were then isolated by column chromatography or preparative thin layer chromatography ("TLC") using n-hexane/ethyl acetate (3:1, v/v) as an eluent. Isolated products were characterized by $^1$H NMR and GC-MS, with spectra matching those reported in the literature or authentic samples.

Hydrogenation with Added Hg

Under nitrogen, complex 1 (6.1 mg, 10.0 μmol) and $H[BAr^F_4].(Et_2O)_2$ (10.1 mg, 10.0 μmol) were dissolved in THF (2.0 mL) in a thick-walled glass vessel equipped with a TEFLON stopper and a stir bar. Styrene (52.0 mg, 0.5 mmol) and Hg (606 mg, 3 mmol) were then added and hexamethylbenzene (0.1 mmol) was also added as internal standard. The bottle was degassed by freeze-pump-thaw and charged with 1 atm of hydrogen gas. The resulting solution was stirred at 25° C. for 24 hours, after which time the reaction mixture was exposed to air and diluted with dichloromethane. GC analysis revealed quantitative conversion to ethylbenzene.

Hydrogenation with Added Water

Complex 1 (6.1 mg, 10.0 μmol) and $H[BAr^F_4](Et_2O)_2$ (10.1 mg, 10.0 μmol) were dissolved in a degassed mixture of $THF/H_2O$ (2.0 mL THF containing $H_2O$ (0.9 μL, 50 mol)) in a thick-walled glass vessel equipped with a TEFLON stopcock. Styrene (52.0 mg, 0.5 mmol) was then added and hexamethylbenzene (0.1 mmol) was also added as internal standard. The vessel was degassed by freeze-pump-thaw and charged with 1 atm of hydrogen gas. The resulting solution was stirred at 25° C. for 24 hours, after which time it was exposed to air and diluted with dichloromethane. GC analysis revealed that the yield of ethylbenzene was 99%.

Procedure for the Hydrogenation of Styrene Using 0.05 Mol % Catalyst

Complex 1 (6.1 mg, 10.0 μmol) and $H[BAr^F_4].(Et_2O)_2$ (10.1 mg, 10.0 μmol) were dissolved in THF (10 mL) in a 100 mL thick-walled glass vessel bottle equipped with TEFLON stopcock and a stir bar. Styrene (2.08 g, 20.0 mmol) was then added and hexamethylbenzene (6.0 mmol) was also added as internal standard. The bottle was degassed by freeze-pump-thaw and then charged with 1 atm of hydrogen gas ("$H_2$"). The resulting solution was stirred at 25° C. for 28 hours, during which time the reaction bottle was periodically recharged with 1 atm $H_2$ to continue to the reaction. After 28 hours at room temperature, the reaction mixture was exposed to air and diluted with dichloromethane, and GC analysis revealed that the yield of ethylbenzene was 55% with a total turnover number (TON) of 1100.

Isomerization of 1-Octene

In an NMR tube equipped with a resealable TEFLON screw cap, complex 1 (3.8 mg, 6.2 μmol) and $H[BAr^F_4]$. $(Et_2O)_2$ (6.3 mg, 6.2 μmol) were dissolved in THF-$d_8$ (0.4 mL). After recording an initial $^1$H NMR spectrum of the solution, the solution was degassed by freeze-pump-thaw, and then hydrogen (1 atm) was added), and then the reaction mixture was allowed to stand at room temperature for 1 hour, after which time signals corresponding to in situ generated 2 had disappeared from the $^1$H NMR spectrum and a new signal appeared at 0 ppm, corresponding to tetramethylsilane. The hydrogen was removed by subjecting the solution to three consecutive cycles of freeze-pump-thaw, and then 1-octene (194 μL, 1.2 mmol) was added under argon. A $^1$H NMR spectrum was recorded immediately after adding the 1-octene. After 20 minutes at room temperature, a $^1$H NMR spectrum was recorded and the signals from the vinylic hydrogens from 1-octene had disappeared while new signals from the olefinic protons from the internal octene isomers had appeared.

Cross-Over Experiment

In an NMR tube equipped with a resealable TEFLON screw cap, complex 1 (6.1 mg, 10.0 mol) and $H[BAr^F_4]$. $(Et_2O_2)_2$ (10.1 mg, 10.0 μmol) were dissolved in THF-$d_8$ (0.6 mL). An initial $^1$H NMR spectrum of the resulting solution was recorded, after which the solution was degassed by freeze-pump-thaw, and then $H_2$ (1 atm) was added). After 1 hour at room temperature, the signals from in situ generated complex 2 disappeared from the $^1$NMR spectrum of the solution while a new signal appeared at 0 ppm, corresponding to tetramethylsilane. The hydrogen was removed after three consecutive cycles of freeze-pump-thaw. In a second NMR tube equipped with a resealable TEFLON screw cap, 1-pentene (14.0 mg, 0.20 mmol), cyclohexene-$d_{10}$ (18.4 mg, 0.2 mmol) and p-xylene (28.6 mg, 0.29 mmol, internal standard) were dissolved in THF-$d_8$ (0.4 mL) under argon. An initial $^1$H NMR spectrum was recorded of the substrate mixture and the internal standard, and then the two NMR solutions were mixed under argon. $^1$H NMR spectra were recorded at room temperature after 5 min, 30 min, 1 hour, 4 hours and 68 hours. Examination of the $^1$H NMR spectra revealed that complete isomerization of the 1-pentene to 2-pentene occurred within 30 minutes at room temperature. Deuterium from the cyclohexene-do was scrambled into the 2-pentene (resonances corresponding to 2-pentene diminished, as judged by integration against the internal standard) and resonances corresponding to cyclohexene-$d_{10-n}$-$h_n$ grew into the NMR spectrum. The presence of protio-cyclohexene was confirmed by comparison with an authentic cyclohexene sample.

Parallel Experiments: Impact of Temperature and Pressure on Acetophenone Hydrogenation For three parallel reactions, complex 1 (6.1 mg, 10.0 μmol) and $H[BAr^F_4](Et_2O)_2$ (10.1 mg, 10.0 μmol) were dissolved in THF (2.0 mL) in a thick-walled glass vessel equipped with a Teflon stopcock and a stir bar. Acetophenone (60 mg, 0.5 mmol) was then added and hexamethylbenzene (0.1 mmol) was also added as internal standard. The reaction mixture was degassed by freeze-pump-thaw and charged with 1 atm (or 4 atm) of hydrogen gas. The resulting solution was stirred at 25° C. or 60° C. for 4 hours (see Equation 5), and then stopped in order to compare relative reaction rates.

Equation 5

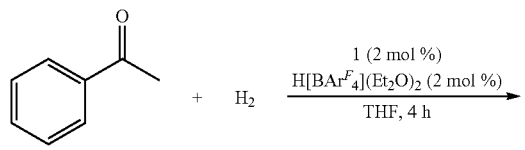

TABLE 4

| Entry | H$_2$/atm | T/° C. | NMR yield (%) |
|---|---|---|---|
| 1 | 1 | 25 | 14 |
| 2 | 1 | 60 | 25 |
| 3 | 4 | 25 | 27 |

Table 5 summarizes data from additional reactions that were performed to explore the scope of hydrogenation reactions.

TABLE 5

| Entry | substrate | product | time (h) | isolated yield (%) (NMR yield) |
|---|---|---|---|---|
| 1[b] | (3,3-dimethyl-1-butene) | (2,2-dimethylbutane) | 22 | (80%) |
| 2[b] | (allyl ethyl ether) | (propyl ethyl ether) | 24 | (93%) |
| 3 | (3,5-dimethoxybenzaldehyde) | (3,5-dimethoxybenzyl alcohol) | 48 | 95% (100%) |
| 4[c] | (benzophenone) | (diphenylmethanol) | 45 | 93% (99%) |
| 5[c] | (4,4'-dimethylbenzophenone) | (bis(4-methylphenyl)methanol) | 45 | 98% (99%) |
| 6[c] | (fluorenone) | (9-fluorenol) | 48 | 97% (99%) |

-continued

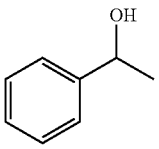

In each case, the solvent was evaporated and the residue was passed through silica gel in a pipette (CH$_2$Cl$_2$ as an eluent), the crude product was evaporated to dryness and the $^1$H NMR spectra recorded in CDCl$_3$. The yields of 1-phenylethanol were determined by integration of the $^1$H NMR spectra against the internal standard. Table 4 below shows results of the parallel experiments.

It is believed that ability to hydrogenate multiple classes of substrates and broad functional group tolerance makes these embodiment cobalt complexes a significant advance over previously reported earth abundant metal complexes for catalytic hydrogenation.

Turning now to nickel complexes, it should be mentioned that square planar complexes [(PNHP$^{iPr}$)Ni(Br)]Br and [(PNHP$^{iPr}$)Ni(NCCH$_3$)](BF$_4$)$_2$ have reported; the latter complex [(PNHP$^{iPr}$)Ni(NCCH$_3$)](BF$_4$)$_2$ was found to catalyze the nucleophilic addition of piperidine to acetonitrile.

Embodiment complexes of nickel, like the embodiment cobalt complexes, may be used for catalytic hydrogenation. Embodiment complexes of nickel similar to those of the cobalt complexes were prepared and used for catalytic alkene hydrogenation under mild conditions. Experiments were performed to gain insight into the hydrogenation mechanism.

Reaction of PNHP$^{Cy}$ with Ni(diglyme)Br$_2$ in THF, followed by recrystallization, afforded the cationic Ni(II) complex [(PNHP$^{Cy}$)Ni(Br)]Br (5) as orange crystals in good yield. Complex 5 was characterized by NMR and IR spectroscopy and elemental analysis. Reaction of complex 5 with NaBH$_4$ in methanol produced [(PNHP$^{Cy}$)Ni(H)]BPh$_4$ (6) (see Scheme 3 below).

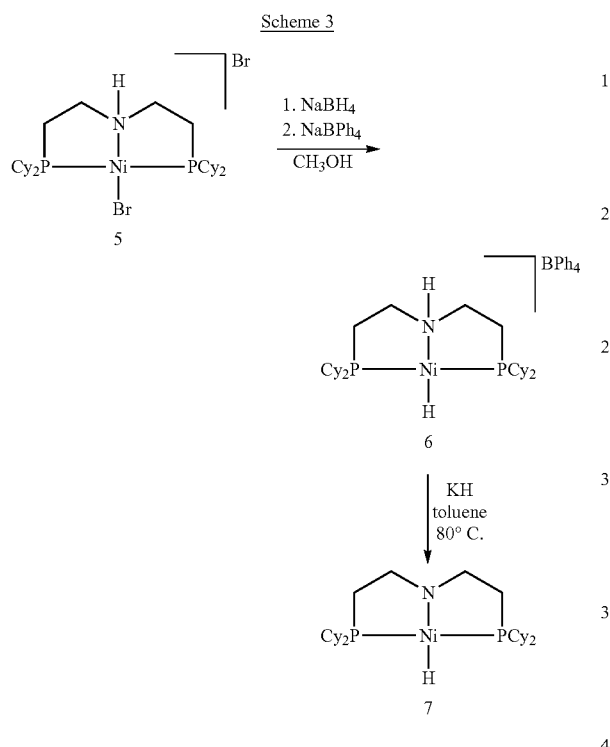

The $^1$H NMR spectrum (CD$_3$CN) of complex 6 shows a triplet hydride signal at −19.59 ppm (J$_{P-H}$=62.2 Hz), and the IR spectrum shows a Ni—H stretch at 1886 cm$^{-1}$. The hexafluorophosphate derivate [(PNHP$^{Cy}$)Ni(H)]PF$_6$ (6-PF$_6$) was prepared by using an analogous procedure (vide infra) and displays very similar NMR features. The X-ray structure of complex 6-PF$_6$ was obtained. The distance between the nickel and the central nitrogen of the pincer ligand (1.978(2) Å) is consistent with the nitrogen being protonated.

The neutral hydride complex (PNP$^{Cy}$)Ni(H) (7) was prepared by deprotonation complex 6 with KH (see Scheme 4).

In the $^1$H NMR spectrum of complex 7 (benzene-d$_6$), the hydride signal appears as a triplet at −17.32 ppm (J$_{P-H}$=62.8 Hz), shifted more than 2 ppm downfield from the hydride signal of complex 6. The IR spectrum of complex 7 shows a Ni—H stretch at 1811 cm$^1$. Single crystals of complex 7 were grown from a concentrated diethyl ether solution. A single crystal X-ray diffraction structure of complex was also obtained. The distance between the nickel and the central nitrogen of the pincer ligand of complex 7 (1.876(2) Å) is significantly shorter than the Ni—N distance of complex 6 (1.978(2) Å).

Cationic complex 6 and neutral complex 7 were evaluated for catalytic hydrogenation.

Turning first to complex 6, heating styrene under hydrogen (1 atm) with complex 6 (10 mol %) in THF-d$_8$ solution produced ethylbenzene in about 10% yield after 5 days at 80° C. Increasing the hydrogen pressure to 4 atm resulted in complete conversion of styrene to ethylbenzene after 24 hours at 80° C. (Scheme 4 and Table 6, entry 1). At the end of the reaction, the only nickel species detected in the solution by $^1$H and $^{31}$P NMR spectroscopy was complex 6.

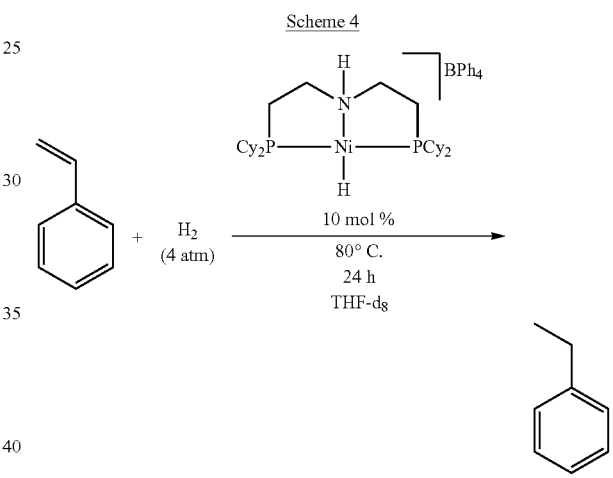

To test for the possible formation of an active colloidal or nanoparticle Ni catalyst, the hydrogenation of styrene using complex 6 (10 mol %) was conducted with stirring in the presence of excess Hg metal (390 equiv). The hydrogenation of styrene was unaffected by the addition of Hg, suggesting that the active catalytic species is homogeneous. The hydrogenation reaction mixtures maintained a clear, pale yellow appearance throughout the reaction, with no evident formation of nickel metal.

TABLE 6 [a]

| Entry | Substrate | Product | Time (hours) | Yield (%) [b] |
|---|---|---|---|---|
| 1 | styrene | ethylbenzene | 24 | 100 |
| 2 | 1-decene | decane | 24 | 70 |

TABLE 6 [a]-continued

| Entry | Substrate | Product | Time (hours) | Yield (%) [b] |
|---|---|---|---|---|
| 3 | (3,3-dimethyl-1-butene) | (neohexane) | 48 | 97 |
| 4 | (α-methylstyrene) | (isopropylbenzene) | 48 | 48 |
| 5 | (3,5-dimethoxybenzaldehyde) | (3,5-dimethoxybenzyl alcohol) | 24 | 5 |
| 6 | (cinnamaldehyde) | (3-phenyl-1-propanol) | 24 | 10 |

[a] Conditions: 80° C., 4 atm $H_2$, THF-$d_8$ solvent.
[b] Yields were determined by $^1$H NMR spectroscopy (integration against an internal standard) and verified by GC-MS.

Complex 6 was also tested for the hydrogenation of several other substrates. Heating 1-octene with complex 6 (10 mol %) under 4 atm $H_2$ (THF-$d_8$ solvent, 80° C., 24 hours) produced n-octane (70%) and internal octene isomers (30%, arising from isomerization of the 1-octene) (Table 6, entry 2). Prolonging the reaction time to 48 hours resulted in a higher yield (76%) of n-octane. Internal octene isomers (24%) remained at the end of the reaction, indicating that the terminal 1-octene is hydrogenated more rapidly than its internal isomers. The more sterically hindered olefins 3,3-dimethyl-1-butene and α-methylstyrene were also hydrogenated under the same reaction conditions (4 atm $H_2$, 80° C.), albeit somewhat more slowly, affording neohexane (97%) and isopropylbenzene (48%) after 48 hours (Table 6, entries 3 and 4).

Lower conversions resulted from hydrogenation of aldehyde substrates using complex 6. Heating a THF-$d_8$ solution of 3,5-dimethoxybenzaldehyde under 4 atm $H_2$ with complex 6 (10 mol %) afforded 3,5-dimethoxybenzylalcohol in 5% yield (Table 6, entry 5). The identity of the 3,5-dimethoxybenzylalcohol was confirmed by spiking the reaction mixture with the authentic compound. 3,5-Dimethoxybenzoic acid was not detected in the reaction mixture by $^1$H NMR spectroscopy, suggesting that the 3,5-dimethoxybenzyl alcohol was formed from the hydrogenation of the aldehyde, and not by aldehyde disproportionation. When the hydrogenation of cinnamaldehyde was performed under the same reaction conditions (4 atm $H_2$, 80° C., 24 hours), 3-phenyl-1-propanol was formed in 10% yield (Table 6, entry 6).

We believe that the reactions above, which relate to hydrogenation of C=O and C=C groups that involve complex 6, are unusual because of the relatively mild reaction conditions.

Turning now to complex 7, heating a benzene-$d_6$ solution of styrene under 4 atm $H_2$ with complex 7 (10 mol %) resulted in a 30% yield of ethylbenzene after 24 hours at 80° C. A somewhat higher conversion was observed in the hydrogenation of 1-octene using 7 (10 mol %), which afforded a mixture of n-octane (76%) and internal octene isomers (24%) after 24 hours at 80° C. No hydrogenation of 3,5-dimethoxybenzaldehyde or cinnamylaldehyde was observed using complex 7.

Experiments were performed to try to understand the reaction mechanism for hydrogenation using complex 6. For example, addition of excess of 1-octene to a benzene-$d_8$ solution of 6-PF$_6$ resulted in complete conversion to the complex [(PNHP$^{Cy}$)Ni(CH$_2$(CH$_2$)$_6$CH$_3$)]PF$_6$ (8-PF$_6$) after 4 days at 25° C. (Scheme 5).

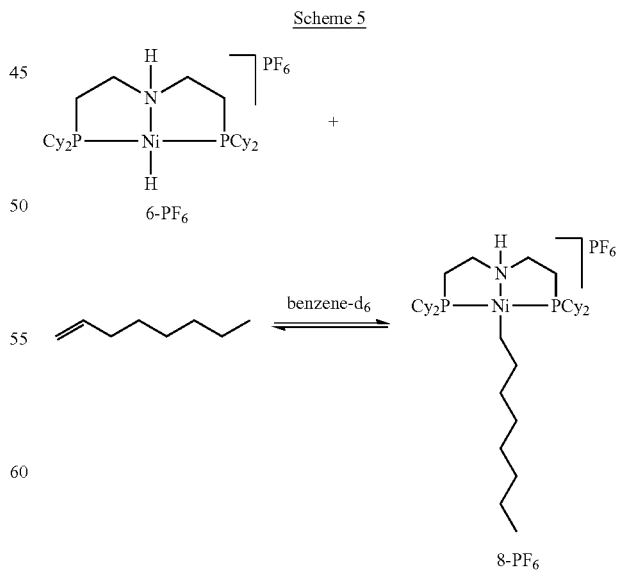

Scheme 5

Complex 8-PF$_6$ was isolated and characterized by NMR and IR spectroscopy. The $^{13}$C{$^1$H} NMR spectrum of 8-PF$_6$ included a triplet ($J_{F-C}$=21 Hz) at −2.2 ppm for the carbon bound to the Ni center. The DEPT-135 NMR spectrum of 8-PF$_6$ confirmed a 1,2-insertion of 1-octene into the Ni—H bond of 2-PF$_6$. The preference for a 1,2-insertion rather than a 2,1-insertion are likely due to steric interactions between 1-octene with the bulky cyclohexyl-substituted phosphines from the pincer ligand.

Insertion of 1-octene into the Ni—H bond of 6 was found to be reversible. An isolated sample of complex 8-PF$_6$ was heated in benzene-d$_6$ solution (80° C.) in the absence of 1-octene to afford complex 6-PF$_6$ (80%), 1-octene (47%), and internal octene isomers (30%). An isolated sample of complex 8 was heated in THF-d solution under hydrogen (4 atm). After 2 hours at 80° C., 90% conversion of complex 8 had occurred, affording complex 6, 1-octene (64%), and n-octane (25%). Besides showing the reversibility of the insertion, the above results also suggest that n-hydride elimination occurs more rapidly than alkane product release from complex 8.

The deuteride complex [(PNDP$^{Cy}$)Ni(D)]PF$_6$ (6-d$_2$) was prepared, and a benzene-d$_6$ solution of 6-d$_2$ was treated with H$_2$ (1 atm). H-D gas was detected by $^1$H NMR spectroscopy within 10 minutes at room temperature (Scheme 6), and the resonances corresponding to the Ni—H and N—H grew into the $^1$H NMR spectrum of complex 6 over the course of 24 hours (25° C.).

Scheme 6

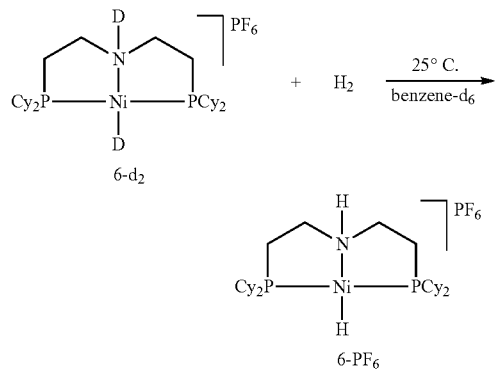

The formation of the H-D gas suggests a reaction mechanism in which H$_2$ gas adds to the cationic nickel(II) center of 6-d$_2$, as opposed to a mechanism involving elimination of D$_2$ from 6-d$_2$ followed by reaction with H$_2$, which would not be expected to form H-D.

Treatment of complex 6 with 50 equivalents of styrene resulted in approximately 85% conversion to the insertion product [(PNHP$^{Cy}$)Ni(CH$_2$CH$_2$Ph)]BPh$_4$ (9), which was identified by its $^1$H, $^{13}$C{$^1$H}, and DEPT-135 NMR spectra (THF-d$_8$) recorded in the presence of excess styrene. The $^{13}$C{$^1$H} NMR spectrum of 9 generated in situ showed a triplet signal for the carbon bound to the nickel center at 0.35 ppm ($J_{P-C}$=20 Hz). By contrast, when a THF-d$_8$ solution of complex 6 and 10 equivalents of 3,5-dimethoxybenzaldehyde was heated at 80° C. for 24 hours, no apparent reaction had occurred.

Details related to the synthesis of several non-limiting embodiments of complexes of nickel as well as several non-limiting embodiment hydrogenation reactions are provided in the EXAMPLES below. Unless specified otherwise, all reactions were carried out under a dry argon atmosphere using standard glove-box and Schlenk techniques. Deuterated solvents were purchased from CAMBRIDGE ISOTOPE LABORATORIES. Benzene-d$_6$ and THF-d$_8$ were dried over Na metal, CD$_3$CN and CD$_2$Cl$_2$ were dried over CaH$_2$, and CDCl$_3$ was used as received. 1-Octene was dried over sodium metal, and styrene was dried over CaH$_2$. Anhydrous grade THF, pentane, benzene, toluene, and diethyl ether were obtained from ALDRICH or ACROS and stored over 4 Å molecular sieves. Bis[2-(dicyclohexylphosphino)ethyl]amine was purchased from STREM CHEMICAL, and nickel(II) bromide 2-methoxyethyl ether complex (Ni(diglyme)Br$_2$) was purchased from ALDRICH. $^1$H, $^{13}$C, and $^{31}$P NMR spectra were obtained at room temperature on a BRUKER AV400 MHz spectrometer, with chemical shifts (δ) referenced to the residual solvent signal ($^1$H and $^{13}$C) or referenced externally to H$_3$PO$_4$ (0 ppm). GC-MS analysis was obtained using a Hewlett Packard 6890 GC system equipped with a HEWLETT PACKARD 5973 mass selective detector. Elemental analyses were performed by ATLANTIC MICROLAB (Norcross, Ga.).

Examples with Complexes of Nickel

Synthesis of [(PNHP$^{Cy}$)Ni(Br)]Br (5). In a vial, PNHP$^{Cy}$ (91.5 mg, 0.197 mmol) and Ni(diglyme)Br$_2$ (65.0 mg, 0.185 mmol) were combined in THF (4 mL), and the orange reaction mixture was stirred for 18 hours at room temperature. Methanol (3 mL) was added, and then the mixture was filtered through a TEFLON syringe filter. The filter was washed with methanol (2 mL), the solution and filtrate were combined, and the solvent removed under vacuum. The resulting orange residue was recrystallized from methylene chloride/diethyl ether, affording orange crystals of complex 6. The crystals were washed with diethyl ether (2×3 mL), and dried under vacuum. Yield of complex 5: 117 mg (87%). $^1$H NMR (400 MHz, CDCl$_3$) δ 6.90 (br s, 1H, NH), 3.21-3.12 (m, 2H, PNP), 2.46-2.43 (m, 2H, PNP), 2.35-2.16 (m, 10H, PNP), 2.04-1.89 (m, 14H, PNP), 1.82-1.58 (m, 12H, PNP), 1.43-1.28 (m, 12H, PNP). $^{13}$C{$^1$H} NMR (100 MHz, CDCl$_3$): 54.8 (vt, $J_{P-C}$=5 Hz), 34.3 (vt, $J_{P-C}$=11 Hz), 33.5 (vt, $J_{P-C}$=12 Hz), 29.5 (s), 28.5 (s, 2C), 28.4 (s), 27.4-26.8 (m, 4C), 26.2 (s), 26.0 (s), 21.9 (vt, $J_{P-C}$=9 Hz). $^{31}$P{$^1$H} NMR (162 MHz, CDCl$_3$): 49.0 (s). IR (thin film): $v_{N-H}$=3402 cm$^{-1}$. Anal. Calcd for C$_{28}$H$_{53}$Br$_2$NNiP$_2$:C, 49.15; H, 7.81; N, 2.05. Found: C, 49.61; H, 7.89; N, 1.96.

Synthesis of [(PNHP$^{Cy}$)Ni(H)]BPh$_4$ (6-BPh$_4$)

In a vial, complex 5 (54.0 mg, 0.0818 mmol) was dissolved in methanol (8 mL) by stirring at room temperature. A total of 15.3 mg NaBH$_4$ (15.3 mg, 0.403 mmol) was added in two portions to the solution. The solution changed color from orange to a lighter yellow color and bubbled vigorously. In a separate vial, NaBPh$_4$ (32.6 mg, 0.0953 mmol) was dissolved in methanol (1 mL). Once the bubbling subsided, the solution of NaBPh$_4$ was carefully layered on top of the reaction mixture, and allowed to stand at room temperature for 2 hours, during which time light golden-colored crystals formed. The supernatant was removed by pipette and the crystals washed with diethyl ether (2×3 mL) and dried under vacuum. Yield of complex 6-BPh$_4$: 60.9 mg (84%). $^1$H NMR (400 MHz, CD$_3$CN) δ 7.29-7.25 (m, 8H, BPh$_4$), 6.99 (t, 8H, J=7.2 Hz, BPh$_4$), 6.84 (t, 4H, J=7.2 Hz, BPh$_4$), 3.90 (br s, 1H, NH), 3.25-3.11 (m, 2H, PNP), 2.41-2.31 (m, 2H, PNP), 2.19-2.00 (m, 6H, PNP), 1.99-1.69 (m, 20H, PNP), 1.48-1.18 (m, 22H, PNP), −19.59 (t, 1H, $J_{P-C}$=62.2 Hz, Ni—H). $^{13}$C {H} NMR (100 MHz, CD$_3$CN): 164.9 (q, $J_{B-C}$=49 Hz), 136.8 (s), 126.7 (q, $J_{B-C}$=3 Hz), 122.9 (s), 52.2 (vt, $J_{P-C}$=4 Hz), 34.3 (vt, $J_{B-C}$=12 Hz), 33.5 (vt, $J_{P-C}$=14 Hz), 30.8 (s), 30.7 (s), 29.8 (s), 27.6-27.2 (m, 4C), 26.9 (s), 26.8 (s), 24.8 (vt, $J_{P-C}$=9 Hz). $^{31}P\{^{1}H\}$ NMR (162 MHz, CD$_3$CN): 56.4 (s). IR (thin film): $v_{N-H}$=3187 cm$^{-1}$, $v_{N-H}$=1886 cm$^{-1}$. Anal. Calcd for C$_{52}$H$_{74}$BNNiP$_2$:C, 73.95; H, 8.83; N, 1.66. Found: C, 74.02; H, 8.92; N, 1.71.

Synthesis of [(PNHP$^{Cy}$)Ni(H)]PF$_6$ (6-PF$_6$)

In a small vial, complex 5 (36 mg, 0.052 mmol) and NaBH$_4$ (12 mg, 0.32 mmol) were suspended in THF (3 mL). Methanol (1 mL) was added dropwise until the suspension began to bubble vigorously. The pale yellow mixture was allowed to react at room temperature for 20 minutes, during which time the bubbling ceased. At this time, KPF$_6$ (16 mg, 0.087 mmol) was added, and the reaction mixture stirred for 10 minutes. The solvent was removed under vacuum, leaving an off-white residue. The residue was extracted with benzene (2×2 mL), and filtered through a glass wool pipette. The benzene was removed under vacuum, leaving a nearly colorless residue. Yield of complex 6-PF$_6$: 28 mg (80%). Crystals suitable for X-ray diffraction were obtained by diffusion of diethyl ether into a toluene solution of 6-PF$_6$ at −20° C. $^1$H NMR (400 MHz, benzene-d$_6$) δ 4.32 (br s, 1H, NH), 3.21-3.12 (m, 2H, PNP), 2.46-2.43 (m, 2H, PNP), 2.35-2.16 (m, 10H, PNP), 2.04-1.89 (m, 14H, PNP), 1.82-1.58 (m, 12H, PNP), 1.43-1.28 (m, 12H, PNP), −19.36 (t, 1H, $J_{P-H}$=61.2 Hz, Ni—H). $^{13}$C $\{^1H\}$NMR (100 MHz, benzene-d$_6$): 52.6 (vt, $J_{P-C}$=5 Hz), 34.1 (vt, $J_{P-C}$=13 Hz), 33.4 (vt, $J_{P-C}$=14 Hz), 30.5 (s), 30.0 (s), 29.3 (s), 28.8 (s), 27.4-27.0 (m, 4C), 26.7 (s), 26.5 (s), 24.4 (vt, $J_{P-C}$=9 Hz). $^{31}P\{^{1}H\}$ NMR (162 MHz, benzene-d$_6$): 55.2 (s), −142.6 (h, $J_{F-P}$=713 Hz). IR (thin film): $v_{N-H}$=3232 cm$^{-1}$, $v_{Ni-H}$=1886 cm$^{-1}$.

Synthesis of (PNP$^{Cy}$)Ni(H) (7)

To a 15 mL thick-walled glass tube was added 6-BPh$_4$ (15 mg, 0.018 mmol) and KH (11 mg, 0.274 mmol). The solids were suspended in toluene (7 mL), the vessel sealed, and the mixture stirred at 80° C. for 15 hours. The resulting brown suspension was filtered through a PTFE syringe filter and the toluene removed under vacuum, affording a dark yellow oil. Yield of complex 7: 7.5 mg (80%). $^1$H NMR (400 MHz, benzene-d$_6$) δ 3.48-3.40 (m, 4H, PNP), 2.18-2.14 (m, 4H, PNP), 2.04-2.00 (m, 4H, PNP), 1.90-1.68 (m, 20H, PNP), 1.62-1.12 (m, 20H, PNP), −17.32 (t, 1H, $J_{P-H}$=62.8 Hz, Ni—H). $^{13}$C$\{^1H\}$ NMR (100 MHz, benzene-d$_6$): 59.7 (vt, $J_{F-C}$=7 Hz), 34.9 (vt, $J_{F-C}$=12 Hz), 30.5 (vt, $J_{F-C}$=2 Hz), 29.2, 27.8-27.6 (m, 2C), 27.4 (vt, $J_{P-C}$=9 Hz), 27.1. $^{31}P\{^{1}H\}$ NMR (162 MHz, benzene-d$_6$): 73.8 (s). IR (thin film): $v_{Ni-H}$=1811 cm$^{-1}$.

Isolation of [(PNHP$^{Cy}$)Ni(CH$_2$(CH$_2$)$_6$CH$_3$)]PF$_6$ (8-PF$_6$)

Complex 6-PF$_6$ (8.4 mg, 0.013 mmol) was dissolved in benzene-d$_6$ (0.6 mL). 1-Octene (0.050 g, 0.45 mmol) was added and the resulting solution was allowed to stand at room temperature for 4 days, after which time examination of the $^1$H and $^{31}$P NMR spectra of the reaction mixture revealed that complete conversion to 4-PF$_6$ had occurred. Addition of pentane (2 mL) and diethyl ether (1 mL) afforded a pale tan precipitate, which was washed with pentane (1 mL) and dried under vacuum. Yield of 8-PF$_6$: 3.2 mg (31%). $^1$H NMR (400 MHz, benzene-d$_6$) δ 3.42-3.22 (m, 3H, N-H and PNP), 2.12-2.03 (m, 8H, PNP), 1.91-1.56 (m, 28H, PNP and octyl), 1.44-1.07 (m, 29H, PNP and octyl), 0.76 (m, 2H, octyl). $^{13}$C$\{^1H\}$ NMR (100 MHz, benzene-d$_6$): 52.1 (vt, $J_{P-C}$=5 Hz), 35.2 (s), 34.8 (vt, $J_{P-C}$=10 Hz), 33.4 (vt, $J_{P-C}$=11 Hz), 32.6 (s), 32.3 (s), 30.4 (s), 30.2 (s), 29.9 (s), 29.2 (s), 28.6, 28.5, 28.0 (vt, $J_{P-C}$=7 Hz), 27.9 (vt, $J_{P-C}$=7 Hz), 27.5 (vt, $J_{P-C}$=4 Hz), 27.3 (vt, $J_{P-C}$=5 Hz), 26.7 (s), 26.6 (s), 23.5 (s), 23.1 (vt, $J_{P-C}$=10 Hz), 14.7 (s), −2.2 (t, $J_{P-C}$=21 Hz). $^{31}P\{^{1}H\}$ NMR (162 MHz, benzene-d$_6$): 36.2 (s), −142.6 (h, $J_{F-P}$=713 Hz). IR (thin film): $v_{N-H}$=3241 cm$^{-1}$.

Synthesis of [(PNHP$^{Cy}$)Ni(CH$_3$)]BPh$_4$

Complex 7 (24 mg, 0.045 mmol) was dissolved in methanol (2 mL). Upon addition of NaBPh$_4$ (17 mg, 0.050 mmol), a pale yellow precipitate formed immediately. The solid was allowed to settle, the supernatant removed by pipette, and the solid washed with methanol (2×2 mL). The yellow solid was dried under vacuum, and then recrystallized from hot toluene. The yellow crystals were washed with pentane (2 mL), and dried under vacuum. Yield of [(PNHP$^{Cy}$)Ni(CH$_3$)]BPh$_4$: 23.5 mg (62%). $^1$H NMR (400 MHz, CD$_2$Cl$_2$) δ 7.35 (m, 8H, BPh$_4$), 7.04 (t, 8H, J=7.2 Hz, BPh$_4$), 6.89 (t, 4H, J=7.2 Hz, BPh$_4$), 2.58-2.44 (m, 2H, PNP), 2.02-1.97 (m, 6H, PNP), 1.90-1.64 (m, 22H, PNP), 1.52-1.23 (m, 22H, PNP), −0.58 (t, 3H, $J_{P-H}$=8.8 Hz, Ni—CH$_3$). $^{13}$C$\{^1H\}$ NMR (100 MHz, CD$_2$Cl$_2$): 164.6 (q, $J_{P-C}$=49 Hz), 136.5 (br s), 126.2 (q, $J_{B-C}$=3 Hz), 122.4 (s), 52.1 (vt, $J_{P-C}$=5 Hz), 34.3 (vt, $J_{P-C}$=11 Hz), 31.2 (vt, $J_{P-C}$=12 Hz), 29.7 (s), 29.5 (s), 29.1 (s), 28.6 (s), 27.7-27.5 (m, 2C), 27.3 (vt, $J_{P-C}$=6 Hz), 27.2 (vt, $J_{P-C}$=6 Hz), 26.6 (s), 26.5 (s), 23.6 (vt, $J_{P-C}$=9 Hz), −21.9 (t, $J_{P-C}$=24 Hz). $^{31}P\{^{1}H\}$ NMR (162 MHz, CD$_2$Cl$_2$): 40.2 (s). IR (thin film): $v_{N-H}$=3183 cm$^{-1}$. Anal. Calcd for C$_{53}$H$_{76}$BNNiP$_2$:C, 74.14; H, 8.92; N, 1.63. Found: C, 73.19; H, 8.76; N, 1.63.

Synthesis of (PNP$^{Cy}$)Ni(Br)

A mixture of complex 5 (105 mg, 0.159 mmol) and NaOCH$_3$ (34 mg, 0.63 mmol) was prepared in THF (3 mL) and stirred at room temperature for 45 minutes, during which time the color changed from orange to dark green. Filtration through a glass wool pipette followed by solvent removal afforded a dark green residue that was treated with toluene (1 mL). The solvent was removed under vacuum, affording a dark green oil. Diethyl ether (1 mL) was added, and the solvent removed under vacuum, leaving a dark green microcrystalline solid of (PNP$^{Cy}$)Ni(Br). Yield: 83 mg (87%). $^1$H NMR (400 MHz, benzene-d$_6$) δ 2.71-2.59 (m, 6H, PNP), 2.12-2.07 (m, 4H, PNP), 1.92-1.54 (m, 28H, PNP), 1.30-1.12 (m, 14H, PNP). $^{13}$C $\{^1H\}$ NMR (100 MHz, benzene-d$_6$): 61.6 (vt, $J_{P-C}$=6 Hz), 33.9 (vt, $J_{P-C}$=11 Hz), 29.6 (s), 28.7 (s), 27.8 (vt, $J_{P-C}$=6 Hz), 27.6 (vt, $J_{P-C}$=5 Hz), 27.0 (s), 23.7 (vt, $J_{P-C}$=10 Hz). $^{31}P\{^{1}H\}$ NMR (162 MHz, CDCl$_3$): 58.8 (s). Anal. Calcd for C$_{28}$H$_{52}$BrNNiP$_2$:C, 55.75; H, 8.69; N, 2.32. Found: C, 55.88; H, 8.84; N, 2.37.

Synthesis of (PNP$^{Cy}$)Ni(CH$_3$)

In a small vial, (PNP$^{Cy}$)Ni(Br) (41 mg, 0.068 mmol) was suspended in diethyl ether (2 mL). Methyl lithium (50 μL of a 1.6 M solution in diethyl ether, 0.08 mmol) was added dropwise at room temperature, the color changing from dark green to bright orange. The reaction mixture was allowed to stand for 5 minutes, and then the solvent was removed under vacuum. The orange residue was extracted with pentane (2×2 mL), and then filtered through a glass wool pipette. The pentane was removed under vacuum, affording an orange oil. Yield of (PNP$^{Cy}$)Ni(CH$_3$): 33 mg (90%). $^1$H NMR (400 MHz, benzene-d$_6$) δ 3.31-3.23 (m, 4H, PNP), 2.23-2.19 (m, 4H, PNP), 1.95-1.86 (m, 12H, PNP), 1.76-1.14 (m, 32H, PNP), −0.49 (t, 3H, $J_{P-H}$=8.8 Hz, Ni—CH$_3$). $^{13}$C {$^1$H} NMR (100 MHz, benzene-d$_6$): 59.7 (br s), 33.7 (vt, $J_{P-C}$=11 Hz), 29.7 (s), 28.7 (s), 28.0 (vt, $J_{P-C}$=6 Hz), 27.7 (vt, $J_{P-C}$=5 Hz), 27.2 (s), 26.5 (vt, $J_{B-C}$=10 Hz), −25.0 (t, $J_{P-C}$=24 Hz). $^{31}$P {$^1$H} NMR (162 MHz, benzene-d$_6$): 59.2 (s).

General Procedure for the Hydrogenation Reactions

In a WILMAD pressure NMR tube, complex 6 (ca. 5 mg, 0.006 mmol) was dissolved in THF-d$_8$ (0.4 mL) containing hexamethylbenzene added as an internal standard. The appropriate substrate (0.06 mmol) was added, and after recording an initial $^1$H NMR spectrum, the solvent was frozen and the headspace of the tube was evacuated. The tube was then submersed in a dewar vessel that contained liquid nitrogen to a level just under the TEFLON seal, and H$_2$ (1 atm) was added. The tube was sealed while still cold, and then allowed to warm to room temperature, which resulted in a pressure of approximately 4 atm (the tube headspace was measured to be 2 mL, containing ~0.34 mmol H$_2$). The tube was heated at 80° C. and the reaction monitored by $^1$H and $^{31}$P NMR spectroscopy. At the end of the reaction, the product yields were determined by $^1$H NMR (integration vs. the internal standard) and verified by GC-MS (comparison of retention time and mass to authentic samples). Hydrogenations with complex 7 were conducted using an analogous procedure in benzene-d$_6$ solvent.

In summary, transition metal complexes of nickel or cobalt were used with hydrogen for the catalytic hydrogenation of unsaturated compounds. The complexes included a pincer ligand that may play a role in promoting the reaction.

Although the present invention has been described with reference to various embodiments and specific details, it is not intended that such embodiments and details should be regarded as limitations upon the scope except as and to the extent that they are included in the accompanying claims.

What is claimed is:

1. A composition of the formula

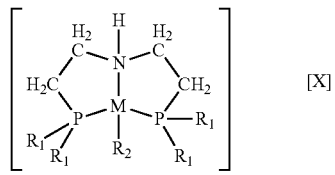

wherein each R$_1$ is independently selected from cycloalkyl, alkyl, substituted alkyl, phenyl, or substituted phenyl;
wherein R$_2$ is —CH$_2$Si(CH$_3$)$_3$, H, alkyl, substituted alkyl, phenyl, substituted phenyl, alkoxide, or amido;
wherein M is cobalt or nickel; and
wherein X is a counterion.

2. The composition of claim 1, wherein the counterion X is tetraphenylborate, hexafluorophosphate, B(C$_6$F$_5$)$_4$, or B(3,5-(CF$_3$)$_2$C$_6$H$_3$)$_4$.

3. The composition of claim 2, wherein M is cobalt, R$_2$ is —CH$_2$Si(CH$_3$)$_3$, and X is B(3,5-(CF$_3$)$_2$C$_6$H$_3$)$_4$.

4. The composition of claim 2, wherein M is cobalt, R$_2$ is H, and X is B(3,5-(CF$_3$)$_2$C$_6$H$_3$)$_4$.

5. The composition of claim 2, wherein M is cobalt, R$_2$ is alkyl, and X is B(3,5-(CF$_3$)$_2$C$_6$H$_3$)$_4$.

6. The composition of claim 2, wherein M is nickel, R$_2$ is H, and X is tetraphenylborate, hexafluorophosphate, or B(3,5-(CF$_3$)$_2$C$_6$H$_3$)$_4$.

7. A composition of the formula

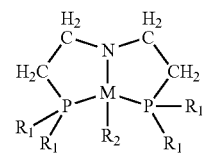

wherein each R$_1$ is independently selected from cycloalkyl, alkyl, substituted alkyl, phenyl, or substituted phenyl;
wherein R$_2$ is —CH$_2$Si(CH$_3$)$_3$, H, alkyl, substituted alkyl, phenyl, substituted phenyl, alkoxide, or amido; and
wherein M is cobalt or nickel.

8. The composition of claim 6, wherein M is cobalt and R$_2$ is —CH$_2$Si(CH$_3$)$_3$.

9. The composition of claim 6, wherein M is nickel and R$_2$ is H.

10. A process for hydrogenation of an unsaturated compound, the process comprising:
combining the composition of claim 1 with hydrogen and an unsaturated compound under conditions effective for the hydrogenation of the unsaturated compound.

11. The process of claim 10, wherein M is cobalt.

12. The process of claim 11, wherein R$_2$ is H.

13. The process of claim 12, wherein the counterion X is B(3,5-(CF$_3$)$_2$C$_6$H$_3$)$_4$.

14. The process of claim 11, wherein M is nickel.

15. The process of claim 14, wherein X is B(3,5-(CF$_3$)$_2$C$_6$H$_3$)$_4$.

16. The process of claim 10, wherein the unsaturated compound comprises a carbon-carbon double or triple bond that becomes hydrogenated as a result of the process.

17. The process of claim 10, wherein the unsaturated compound comprises a carbon-oxygen double bond that becomes hydrogenated as a result of the process.

18. The process of claim 10, wherein the unsaturated compound comprises a carbon-nitrogen double or triple bond that becomes hydrogenated as a result of the process.

19. A process for hydrogenation of an unsaturated compound, the process comprising combining a solution of the composition of claim 1 with hydrogen and an unsaturated compound under conditions effective for the hydrogenation of the unsaturated compound.

* * * * *